US009987330B2

(12) United States Patent
Hoon et al.

(10) Patent No.: US 9,987,330 B2
(45) Date of Patent: Jun. 5, 2018

(54) METHODS OF TREATING OR PREVENTING PRURITIS BY BLOCKING NATRIURETIC POLYPEPTIDE B

(71) Applicant: The United States of America, as represented by the Secretary, Department of Health and Human Services, Washington, DC (US)

(72) Inventors: Mark A. Hoon, Kensington, MD (US); Santosh K. Mishra, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days. days.

(21) Appl. No.: 15/039,982

(22) PCT Filed: Dec. 4, 2014

(86) PCT No.: PCT/US2014/068541
§ 371 (c)(1),
(2) Date: May 27, 2016

(87) PCT Pub. No.: WO2015/085055
PCT Pub. Date: Jun. 11, 2015

(65) Prior Publication Data
US 2017/0014486 A1    Jan. 19, 2017

Related U.S. Application Data

(60) Provisional application No. 61/912,334, filed on Dec. 5, 2013.

(51) Int. Cl.
*A61K 38/00* (2006.01)
*A61K 38/10* (2006.01)
*A61K 38/22* (2006.01)
*A01K 67/027* (2006.01)
*C12Q 1/68* (2018.01)
*A61K 38/16* (2006.01)
*C12N 15/85* (2006.01)
*A61K 45/06* (2006.01)
*A61K 38/17* (2006.01)
*C07K 16/26* (2006.01)
*C12N 15/113* (2010.01)
*A61K 47/62* (2017.01)

(52) U.S. Cl.
CPC .......... *A61K 38/22* (2013.01); *A01K 67/0276* (2013.01); *A61K 38/164* (2013.01); *A61K 38/1796* (2013.01); *A61K 38/2242* (2013.01); *A61K 45/06* (2013.01); *A61K 47/62* (2017.08); *C07K 16/26* (2013.01); *C12N 15/1136* (2013.01); *C12N 15/8509* (2013.01); *C12Q 1/6883* (2013.01); *C12Q 1/6886* (2013.01); *A01K 2217/052* (2013.01); *A01K 2217/075* (2013.01); *A01K 2227/105* (2013.01); *A01K 2267/035* (2013.01); *A01K 2267/0393* (2013.01); *C12N 2310/14* (2013.01); *C12Q 2600/136* (2013.01); *C12Q 2600/158* (2013.01); *G01N 2500/02* (2013.01)

(58) Field of Classification Search
None
See application file for complete search history.

(56) References Cited

U.S. PATENT DOCUMENTS 5,449,752 A    9/1995  Fujii et al.
2009/0181896 A1    7/2009  Sharif et al.
2015/0320827 A1*  11/2015  Carstens .............. A61K 31/498
                                                        514/21.7

OTHER PUBLICATIONS

International Bureau, International Search Report in International Application No. PCT/US2014/068541, dated Jun. 17, 2015.
International Bureau, Written Opinion in International Application No. PCT/US2014/068541, dated Jun. 16, 2015.
Aagaard et al. "A Facile Lentiviral Vector System for Expression of Doxycycline-Inducible shRNAs: Knockdown of the Pre-miRNA Processing Enzyme Drosha," *Mol. Ther.*, 15(5): 938-45 (2007).
Adler et al., "A Novel Family of Mammalian Taste Receptors," *Cell*, 100:693-702 (2000).
Akiyama et al., "Neural Processing of Itch," *Neuroscience*, 250: 697-714 (2013).
Caterina et al., "Impaired Nociception and Pain Sensation in Mice Lacking the Capsaicin Receptor," *Science*, 288:306 (2000).
Cavanaugh et al., "Distinct subsets of unmyelinated primary sensory fibers mediate behavioral responses to noxious thermal and mechanical stimuli," *PNAS*, 106:9075 (2009).
Fleming et al., "Themajority of dorsal spinal cord gastrin releasing peptide is synthesized locally whereas neuromedin B is highly expressed in pain- and itch-sensing somatosensory neurons," *Mol. Pain*, 8:52 (2012).
Gong et al., "A gene expression atlas of the central nervous system based on bacterial artificial chromosomes," *Nature*, 425:917 (2003).
Han et al., "A subpopulation of nociceptors specifically linked to itch," *Nat. Neurosci.*, 16:174-182 (2012).
Han et al., "Phospholipase Cβ 3 Mediates the Scratching Response Activated by the Histamine H1 Receptor on C-Fiber Nociceptive Neurons," *Neuron*, 52:691-703 (2006).
Hirata et al., "Role of Endogenous Atrial Natriuretic Peptide in DOCA-Salt Hypertensive Rats: Effects of a Novel Nonpeptide Antagonist for Atrial Natriuretic Peptide Receptor," *Circulation*, 87: 554-61 (1993).
Hoon et al., "Putative Mammalian Taste Receptors: A Class of Taste-Specific GPCRs with Distinct Topographic Selectivity," *Cell*, 96:541-51 (1999).

(Continued)

Primary Examiner — Shulamith H Shafer
(74) Attorney, Agent, or Firm — Leydig, Voit & Mayer, Ltd.

(57)  ABSTRACT

Disclosed is a method of treating, reducing, or preventing pruritis in a mammal, the method comprising administering at least one natriuretic polypeptide b (Nppb) blocking agent to a mammal in an amount effective to treat or prevent pruritis in the mammal. An in vitro method of identifying a compound that inhibits Nppb activity is also disclosed.

34 Claims, 7 Drawing Sheets

(56) References Cited

OTHER PUBLICATIONS

Hudecz, F., "Synthesis of Peptide Bioconjugates," *Methods Mol. Biol.* 298: 209-223 (2005).

Imamachi et al., "TRPV1-expressing primary afferents generate behavioral responses to pruritogens viamultiple mechanisms," *PNAS*, 106:11330 (2009).

Kirin et al., "Amino Acid and Peptide Bioconjugates of Copper(Ii) and Zinc(Ii) Complexes with a Modified N,N-Bis(2-picolyl)amine Ligand," *Inorg. Chem*. 44(15): 5405-5415 (2005).

Liu et al., "Sensory Neuron-Specific GPCR Mrgprs Are Itch Receptors Mediating Chloroquine-Induced Pruritus," *Cell*, 139:1353-1365 (2009).

Liu et al., "The Distinct Roles of Two GPCRs, MrgprC11 and PAR2, in Itch and Hyperalgesia," *Science Signaling*, 4(181):ra45 (2011).

McNeil et al., "Peripheral mechanisms of itch," *Neuroscience Bulletin*, 28(2):1 00-110 (2012).

Mishra et al., "A principle neurotransmitter Nppb and its role in itch sensation," abstract from the 43$^{rd}$ Annual Meeting of the Society for Neuroscience, San Diego, CA, Nov. 9-13, 2013.

Mishra et al., "Supplementary Material for 'The Cells and Circuitry for Itch Responses in Mice,'" *Science*, pp. 1-11 (2013).

Mishra et al., "The Cells and Circuitry for Itch Responses in Mice," *Science*, 340(6135): 968-71 (2013).

Mishra et al., "TRPV1-lineage neurons are required for thermal sensation," *EMBO J*., 30:582-93 (2011).

Misono et al., "Structure, signaling mechanism and regulation of the natriuretic peptide receptor guanylate cyclase," *The FEBS Journal*, 278:1818-29 (2011).

Miyoshi et al., "Effect of Natriuretic Peptide Receptor Antagonist on Lipopolysaccharide-Induced Fever in Rats: Is Natriuretic Peptide an Endogenous Antipyretic?" *J. of Pharmacol. And Exp. Ther*., 318(3): 1163-1170 (2006).

Ohyama et al., "HS-142-1, A novel Antagonist for Natriuretic Peptides, Has No Effect on the Third Member of Membrane bound Guanylate Cyclases (GC-C) in T84 Cells," *Life Sciences*, 52: PL153-157 (1993).

Poirier et al., "Allotopic antagonism of the non-peptide atrial natriuretic peptide (ANP) antagonist HS-142-1 on natriuretic peptide receptor NPR-A," *Biochem. J*., 362: 231-237 (2002).

Press Release, "NIH Scientists Discover Molecule Triggers Sensation of Itch," www.nih.govinews/health/may2013/nidcr-23.htm, published May 23, 2013.

Raap et al., "Pathophysiology of itch and new treatments," *Curr. Opin. In Allergy and Clin. Immuno*. 11(5): 420-27 (2011).

Sano et al., "Pharmacological Profile of HS-142-1, A Novel Nonpeptide Atrial Natriuretic Peptide Antagonist of Microbial Origin. I. Selective Inhibition of the Actions of Natriuretic Peptides in Anesthetized Rats," *J. Pharmacol. and Experiment. Therap*., 260(2): 825-831 (1992).

Shim et al., "TRPV1 Mediates Histamine-Induced Itching via the Activation of Phospholipase A2 and 12-Lipoxygenase," *J. Neurosci*., 27:2331 (2007).

Sun et al., "A gastrin-releasing peptide receptor mediates the itch sensation in the spinal cord," *Nature*, 448:700 (2007).

Sun et al., "Cellular Basis of Itch Sensation," *Science*, 325:1531-34 (2009).

Toki et al., "HS-142-1, a novel non-peptide ANP antagonist, blocks the cyclic GMP production elicited by natriuretic peptides in PC12 and NG108-15 cells," *Neurosci. Letters*, 135: 117-120 (1992).

Vilotti et al., "B-Type Natriuretic Peptide-Induced Delayed Modulation of TRPV1 and P2X3 Receptors of Mouse Trigeminal Sensory Neurons," *PLOS ONE*, 8(11): e81138 (2013).

Wiley et al., "Targeted toxins in pain," *Advanced Drug Delivery Reviews*, 55:1043-1054 (2003).

Yegen et al., "Inhibitory effects of gastrin releasing peptide on gastric emptying in rats," *Regulatory Peptides*, 61:175 (1996).

Zhang et al., "HS-142-1, A Potent Antagonist of Natriuretic Peptides In Vitro and In Vivo," *J. Am. Soc. Nephrol*., 5: 1099-1105 (1994).

\* cited by examiner

METHODS OF TREATING OR PREVENTING PRURITIS BY BLOCKING NATRIURETIC POLYPEPTIDE B

CROSS-REFERENCE TO RELATED APPLICATIONS

This patent application is the U.S. national stage of PCT/US2014/068541, filed Dec. 4, 2014, which claims the benefit of U.S. Provisional Patent Application No. 61/912,334, filed Dec. 5, 2013, each of which is incorporated by reference herein in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 48,509 Byte ASCII (Text) file named "724155 ST25.txt," dated May 26, 2016.

BACKGROUND OF THE INVENTION

Itch (also known as pruritis) is a sensation that may be perceived as an unpleasant skin irritation and may drive an urge to scratch. Some itch is transient and is no more than moderately unpleasant. In some cases, however, itch can become chronic, significantly reducing quality of life. Conditions such as, for example, psoriasis, atopic dermatitis, renal failure, liver cirrhosis and some cancers may cause persistent itch. Accordingly, there is a need for improved compositions and methods for treating pruritis.

BRIEF SUMMARY OF THE INVENTION

An embodiment of the invention provides a method of treating, reducing, or preventing pruritis in a mammal, the method comprising administering at least one natriuretic polypeptide b (Nppb) blocking agent (antagonist) to the mammal in an amount effective to treat, reduce, or prevent pruritis in the mammal.

Another embodiment of the invention provides a method of treating, reducing, or preventing pruritis in a mammal, the method comprising administering at least one Nppb blocking agent to the mammal in an amount effective to treat, reduce, or prevent pruritis in the mammal, wherein the Nppb blocking agent is not a Nppb-saporin conjugate.

Still another embodiment of the invention provides an in vitro method of identifying a compound that inhibits Nppb activity, the method comprising: (a) transducing one or more tester cells and one or more control cells with at least one nucleotide sequence encoding a constitutive reporter gene and natriuretic polypeptide receptor A (Npra) comprising a nucleotide cyclase domain, wherein the nucleotide cyclase domain converts adenosine triphosphate (ATP) to cyclic adenosine monophosphate (cAMP) and the constitutive reporter gene is under the transcriptional control of cyclic adenosine monophosphate (cAMP); (b) contacting the tester cells of (a) with a test agent and Nppb; (c) contacting the control cells of (a) with Nppb; (d) incubating the cells; and (e) measuring the amount of reporter gene expression in the cells of (b) and (c), wherein a reduction in reporter gene expression in the cells of (b) as compared to the reporter gene expression in the cells of (c) is indicative of a compound that inhibits Nppb activity.

DETAILED DESCRIPTION OF THE INVENTION

Figure 1:
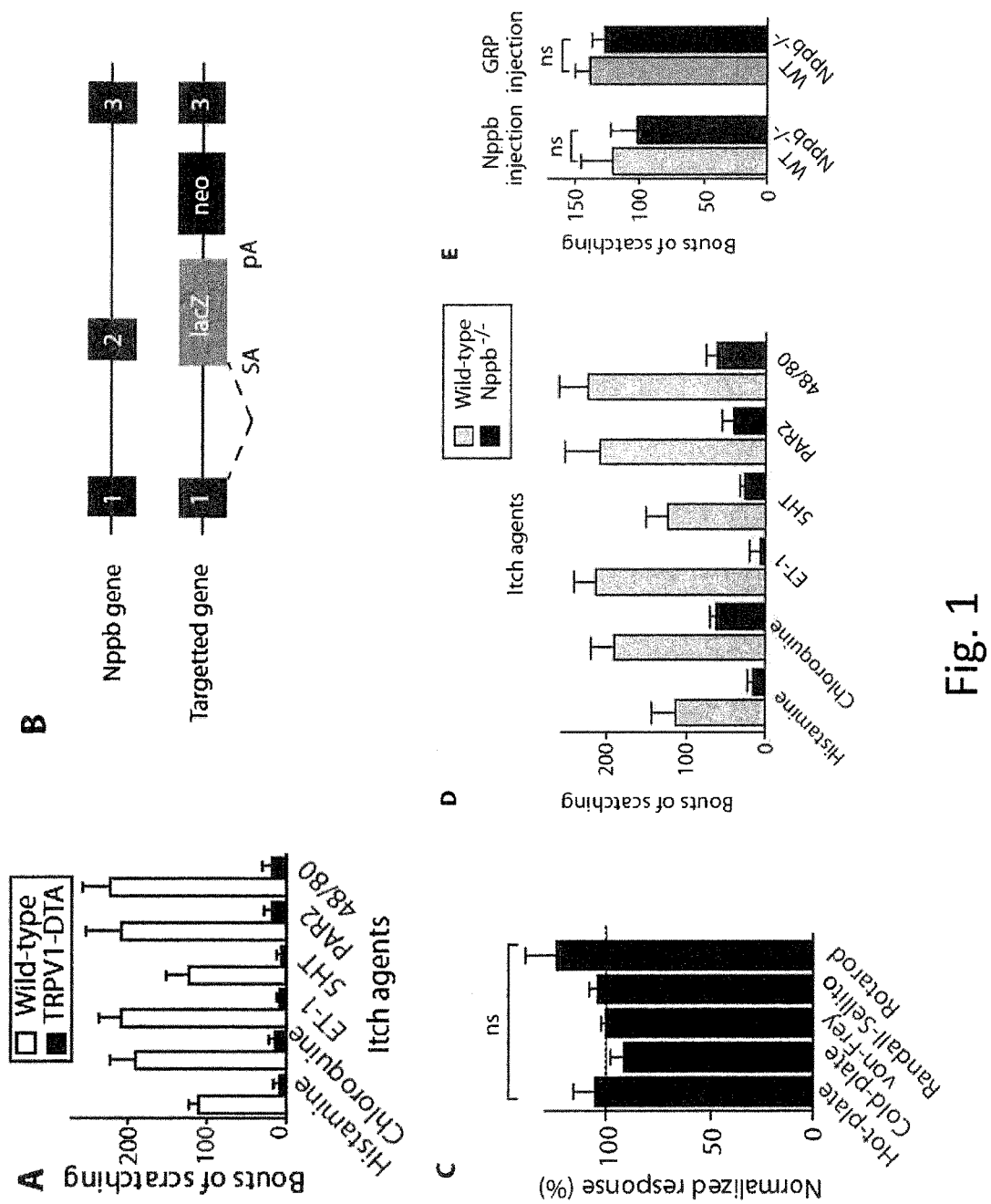
FIG. 1A is a graph showing the numbers of bouts of scratching for wild-type mice (unshaded bars) and TRPV1-DTA mice (shaded bars) after injection with one of itch agents histamine, chloroguine, ET-1, 5HT, PAR2, or 48/80. Data are mean±standard error of the mean (s.e.m) (n≥7 animals) normalized to wild-type litter controls. Behavioral responses in TRPV1-DTA mice were all statistically different from responses of wild-type control animals (Student's t-test, P<0.001).
FIG. 1B is a schematic representation showing the disruption of the Nppb gene by insertion of a splice acceptor-lacZ cassette into the second exon which was used to generate $Nppb^{-/-}$ mice.
FIG. 1C is a graph showing the normalized response (%) of $Nppb^{-/-}$ mice to thermal, nociceptive, touch, and proprioceptive stimulation in standard assays. Data are mean±s.e.m (n≥7 animals) normalized to wild-type litter controls.
FIG. 1D is a graph showing the numbers of bouts of scratching for wild—type and $Nppb^{-/-}$ mice after injection with one of itch agents histamine, chloroguine, ET-1, 5HT, PAR2, or 48/80. For each item on the y-axis, the left bar indicates wild-type, and the right bar indicates $Nppb^{-/-}$ mice. Data are mean±s.e.m (n≥7 animals) normalized to wild-type litter controls. Behavioral responses in Nppb knockout mice were statistically different from responses of wild-type control animals (Student's t-test, P<0.001).
FIG. 1E is a graph showing numbers of bouts of scratching in wild-type or $Nppb^{-/-}$ mice after injection with Nppb or gastrin releasing peptide (GRP). Data represent mean values±s.e.m. (n≥5 animals). "ns"=not significant (Student's T-test).

Natriuretic polypeptide b (Nppb) (also known as brain natriuretic peptide or BNP) is a member of the natriuretic peptide family and encodes a secreted protein which functions as a cardiac hormone. The biological actions of Nppb may include natriuresis, diuresis, vasorelaxation, inhibition of renin and aldosterone secretion, and cardiovascular homeostasis. The Nppb receptor is natriuretic polypeptide receptor A (Npra) (also known as atrial natriuretic peptide receptor A (NPR1)), a membrane-bound guanylate cyclase.

It has been discovered by the inventors of this invention that Nppb is required for pruriception and that administering an Nppb blocking agent treats pruritis. Accordingly, an embodiment of the invention provides a method of treating, reducing, or preventing pruritis in a mammal, the method comprising administering at least one Nppb blocking agent to the mammal in an amount effective to treat, reduce, or prevent pruritis in the mammal.

The pruritis may be transient or chronic. Preferably, the pruritis is chronic.

The pruritis may be caused by or associated with any condition or any treatment of a condition. In an embodiment of the invention, the pruritis may be caused by or associated with a skin condition. Examples of skin conditions may include, but are not limited to, skin infections from *Trichomonas* or a fungus, psoriasis, and atopic dermatitis (also known as eczema). In an embodiment of the invention, the pruritis may be caused by or associated with a systemic condition or treatment of a systemic condition. Examples of systemic conditions may include, but are not limited to, renal failure, liver damage, liver disease (e.g., cirrhosis), acquired immune deficiency syndrome (AIDS), polycythemia vera, diabetes, hyperthyroidism, and cancer (e.g., Hodgkin's lymphoma, non-Hodgkin's lymphoma, and Kaposi's sarcoma). Examples of treatments of systemic conditions include, but are not limited to, kidney dialysis and chemotherapy with agents such as, for example, doxorubicin, daunorubicin, cytarabine, paclitaxel, and cisplatin. These chemotherapeutic agents, which are used to treat a variety of cancers, may cause a skin reaction and may be associated with pruritus. The incidence of non-cancer causes of pruritis may depend on the condition and type of treatment.

The pruritis may be induced by a pruritogen. In an embodiment of the invention, the pruritis is induced by a pruritogen selected from the group consisting of histamine, chloroquine, endothelin (ET-1), 2-methyl serotonin (5HT), SLIGRL-NH2 (PAR2), and compound 48/80 (48/80).

The pruritis may be induced by a cytokine. In an embodiment of the invention, the pruritis is induced or mediated by interleukin (IL)-31. IL-31 is associated with chronic itch in some types of skin disorders such as, for example, atopic dermatitis.

The Nppb blocking agent can be any agent that inhibits or reduces the biological activity of Nppb. The biological activity of Nppb may be inhibited in any manner, e.g., by inhibiting the production (e.g., expression) of any one or more of Nppb mRNA, Nppb protein, Npra mRNA, and Npra protein; by inhibiting the binding of Nppb to Npra, and/or by inhibiting Nppb signaling, as compared to that which is observed in the absence of the Nppb blocking agent. The biological activity may be inhibited to any degree that realizes a beneficial therapeutic effect. For example, in some embodiments, the biological activity may be completely inhibited (i.e., prevented), while in other embodiments, the biological activity may be partially inhibited (i.e., reduced). As used herein, unless stated otherwise, the terms "Nppb" and "Npra" refer to Nppb and Npra, respectively, in any form (e.g., mRNA or protein) and from any species (e.g., human or mouse).

In an embodiment of the invention, the Nppb blocking agent is an agent that inhibits Nppb signaling. Nppb signaling can be inhibited in any manner. For example, the Nppb blocking agent may inhibit the activation of any one or more of various downstream targets of Nppb signaling (e.g., gastrin releasing peptide (GRP)). For example, the Nppb blocking agent may be an agent that binds to the Nppb protein, thereby reducing or preventing Nppb signaling and inhibiting its function. By way of illustration, the agent that inhibits Nppb signaling can be any of the antibodies or antibody fragments, antisense nucleic acids, or chemical inhibitors (e.g., small molecule or peptide (or polypeptide) inhibitor) described herein.

In an embodiment, the Nppb blocking agent is an agent that inhibits the binding of Nppb to the Nppb receptor (Npra). In this regard, the Nppb blocking agent may be an agent that binds to the Nppb protein or the Npra protein, thereby reducing or preventing the binding of the Nppb protein to Npra and inhibiting its function, as well as agents that compete with the Nppb protein for the native Nppb binding site of the Nppb receptor (Npra). By way of illustration, the agent that inhibits the binding of Nppb to Npra can be any of the antibodies or antibody fragments, antisense nucleic acids, or chemical inhibitors (e.g., small molecule or peptide inhibitor) described herein.

In an embodiment of the invention, the Nppb blocking agent is an antibody or antibody fragment that specifically binds to Nppb or Npra. Anti-Nppb and anti-Npra antibodies and antibody fragments can be monoclonal or polyclonal. Anti-Nppb and anti-Npra antibodies and antibody fragments can be prepared using the Nppb and Npra proteins disclosed herein and routine techniques. Examples of such antibodies or antibody fragments include those specific to the native Nppb binding site of the Nppb receptor or a functional domain of Nppb (e.g., the Npra binding portion of Nppb).

Chemical inhibitors of Nppb include small molecules and peptides or polypeptides that inhibit Nppb signaling, bind the Nppb or Npra protein or functional fragment thereof, or compete with the Nppb protein or functional fragment thereof for its native binding site of the Npra. Suitable inhibitors can include, for example, chemical compounds or a non-active fragment or mutant of an Nppb protein. In this regard, in an embodiment of the invention, the Nppb blocking agent is a mutated Nppb. The mutation may include any insertions, deletions, and/or substitutions of one or more amino acids in any position of the Nppb protein that effectively inhibits Nppb biological activity (e.g., Nppb signaling and/or binding of Nppb to Npra). For example, one or more native amino acid residues in the Nppb protein (for example, those involved in receptor binding) may be substituted with amino acid residues containing non-natural side chains and/or D-amino acid residues. For example, the chemical inhibitor can bind to the Npra and/or inhibit Nppb signaling. In this regard, the Nppb blocking agent may be a chemical inhibitor. In a preferred embodiment, the Nppb blocking agent inhibits the activation of gastrin releasing peptide (GRP). Examples of chemical inhibitors include, but are not limited to, anantin, [Asu7,23']b-ANP-(7-28)], HS-142-1, and a combination of any two or more thereof. In a preferred embodiment, the Nppb blocking agent is anantin.

Chemical inhibitors of Nppb can be identified using routine techniques. For example, chemical inhibitors can be tested in binding assays to identify molecules and peptides (or polypeptides) that bind to Nppb or Npra with sufficient affinity to inhibit Nppb biological activity (e.g., binding of Nppb to Npra, and/or Nppb signaling). Also, competition assays can be performed to identify small-molecules and peptides (or polypeptides) that inhibit the activation of downstream targets of Nppb signaling or compete with Nppb or functional fragment thereof for binding to its native binding site of Npra. Such techniques could be used in conjunction with mutagenesis of the Nppb protein or functional fragment thereof itself, and/or with high-throughput screens of known chemical inhibitors. For example, one or more native amino acid residues in the Nppb protein may be randomly substituted with amino acid residues containing non-natural side chains and/or D-amino acids and the mutated proteins can be tested in binding assays to identify mutated proteins that inhibit Nppb biological activity (e.g., binding of Nppb to Npra, and/or Nppb signaling).

The functional fragment of the Nppb or Npra protein can comprise any contiguous part of the Nppb or Npra protein that retains a relevant biological activity of the Nppb or Npra protein, e.g., binds to Npra or Nppb and/or participates in Nppb signaling. Any given fragment of an Nppb or Npra protein can be tested for such biological activity using methods known in the art. For example, the functional fragment can comprise, consist essentially of, or consist of the Npra binding portion of the Nppb protein or the Nppb binding portion of the Npra protein. In reference to the parent Nppb or Npra protein, the functional fragment preferably comprises, for instance, about 10% or more, about 25% or more, about 30% or more, about 50% or more, about 60% or more, about 80% or more, about 90% or more, or even about 95% or more of the parent Nppb protein.

In an embodiment of the invention, the Nppb blocking agent is any suitable agent that inhibits the production (e.g., expression) of any one or more of Nppb mRNA, Nppb protein, Npra mRNA, and Npra protein. The Nppb blocking agent can be a nucleic acid at least about 10 nucleotides in length that specifically binds to and is complementary to a target nucleic acid encoding any one or more of Nppb mRNA, Nppb protein, Npra mRNA, and Npra protein or a complement thereof. The Nppb blocking agent may be introduced into a host cell, wherein the cell is capable of expressing any one or more of Nppb mRNA, Nppb protein, Npra mRNA, and Npra protein, in an effective amount for a time and under conditions sufficient to interfere with production (e.g., expression) of any one or more of Nppb mRNA, Nppb protein, Npra mRNA, and Npra protein, respectively. In some embodiments, RNA interference (RNAi) is employed. In this regard, the Nppb blocking agent may comprise an RNAi agent. In an embodiment, the RNAi agent may comprise a small interfering RNA (siRNA), a short hairpin miRNA (shMIR), a microRNA (miRNA), or an antisense nucleic acid. The RNAi agent, e.g., siRNA, shRNA, miRNA, and/or antisense nucleic acid can comprise overhangs. That is, not all nucleotides need bind to the target sequence. RNA interference nucleic acids employed can be at least about 19, at least about 40, at least about 60, at least about 80, at least about 100, at least about 120, at least about 140, at least about 160, at least about 180, at least about 200, at least about 220, at least about 240, from about 19 to about 250, from about 40 to about 240, from about 60 to about 220, from about 80 to about 200, from about 60 to about 180, from about 80 to about 160, and/or from about 100 to about 140 nucleotides in length.

The RNAi agent, e.g., siRNA or shRNA, can be encoded by a nucleotide sequence included in a cassette, e.g., a larger nucleic acid construct such as an appropriate vector. Examples of such vectors include lentiviral and adenoviral vectors, as well as other vectors described herein with respect to other aspects of the invention. An example of a suitable vector is described in Aagaard et al. *Mol. Ther.*, 15(5): 938-45 (2007). When present as part of a larger nucleic acid construct, the resulting nucleic acid can be longer than the comprised RNAi nucleic acid, e.g., greater than about 70 nucleotides in length. In some embodiments, the RNAi agent employed cleaves the target mRNA. In other embodiments, the RNAi agent employed does not cleave the target mRNA.

Any type of suitable siRNA, miRNA, and/or antisense nucleic acid can be employed. In an embodiment, the antisense nucleic acid comprises a nucleotide sequence complementary to at least about 8, at least about 15, at least about 19, or from about 19 to about 22 nucleotides of a nucleic acid encoding any one or more of Nppb mRNA, Nppb protein, Npra mRNA, and Npra protein or a complement thereof. In an embodiment, the siRNA may comprise, e.g., trans-acting siRNAs (tasiRNAs) and/or repeat-associated siRNAs (rasiRNAs). In another embodiment, the miRNA may comprise, e.g., a short hairpin miRNA (shMIR).

In an embodiment of the invention, the Nppb blocking agent may inhibit or downregulate to some degree the production of the protein encoded by an Npra or Nppb gene, e.g., at the DNA, RNA, or other level of regulation. In this regard, a host cell comprising an Nppb blocking agent expresses none of any one or more of Nppb mRNA, Nppb protein, Npra mRNA, and Npra protein or lower levels of any one or more of Nppb mRNA, Nppb protein, Npra mRNA, and Npra protein as compared to a host cell that lacks an Nppb blocking agent. In accordance with an embodiment of the invention, the Nppb blocking agent, such as an RNAi agent, such as a shMIR, can target a nucleotide sequence of an Nppb or Npra gene or mRNA encoded by the same.

In an embodiment, the Nppb sequence is a human Nppb sequence. For example, human Nppb is assigned Gene NCBI Entrez Gene ID No. 4879, and a Mendelian Inheritance in Man (MIM) No. 600295. The human Nppb gene is found on chromosome 1 at 1p36.2. A transcript includes mRNA GenBank Accession No: NM_002521.2 (SEQ ID NO: 1), with corresponding protein sequence GenBank Accession No: NP_002512.1 (SEQ ID NO: 2). Human genomic Nppb sequences include GenBank Accession Nos: AC_000133.1, NC_018912.2, AB037521.1, ABBA01003061.1, AL021155.1, AMYH02000300.1, CH471130.1, EU326309.1, and M31776.1. Human Nppb mRNA sequences also include Genbank Accession Nos: AJ708502.1, BC025785.1, CR541976.1, CR542003.1, and M25296.1. Human Nppb amino acid sequences include Genbank Accession Nos: BAA90441.1, EAW71718.1, EAW71719.1, ACA05917.1, AAA35603.1, AAH25785.1, CAG46774.1, CAG46800.1, and AAA36355.1. Other human sequences, as well as other Nppb species can be employed in accordance with the invention.

In an embodiment, the Npra sequence is a human Npra sequence. For example, human Npra is assigned Gene NCBI Entrez Gene ID No. 4881, and a Mendelian Inheritance in Man (MIM) No. 108960. The human Npra gene is found on chromosome 1 at 1q21-q22. Two transcriptional variants include mRNA GenBank Accession No: NM_000906.3 (SEQ ID NO: 3) and XM_005245218.1 (SEQ ID NO: 5), with corresponding protein sequence GenBank Accession No: NP_000897.3 (SEQ ID NO: 4) and XP_005245275.1 (SEQ ID NO: 6), respectively. Human genomic Npra sequences include GenBank Accession Nos: AC_000133.1, NC_018912.2, AB010491.2, AB046472.1, ABBA01049444.1, AF190631.1, AL713889.19, AMYH02001904.1, AMYH02001905.1, CH471121.2, and EU326310.1. Human Npra mRNA sequences also include Genbank Accession Nos: AK025024.1, AK298090.1, AK300446.1, BC063304.1, S72628.1, and X15357.1. Human Npra amino acid sequences include Genbank Accession Nos: BAA31199.1, BAC53955.1, AAF01340.1, EAW53284.1, ACA05918.1, ACA05919.1, BAH12723.1, BAG62168.1, AAH63304.1, AAD14112.1, and CAA33417.1. Other human sequences, as well as other Npra species can be employed in accordance with the invention.

In another embodiment, the Nppb sequence is a mouse sequence. For example, mouse Nppb is assigned Gene NCBI Entrez Gene ID No. 18158. The mouse Nppb gene is found on chromosome 4 at 4 E2. A transcript includes mRNA Genbank Accession No.: NM_008726.4 (SEQ ID NO: 7), with corresponding protein sequence NP$_{13}$ 032752.1 (SEQ ID NO: 8). Mouse genomic Nppb sequences include Genbank Accession Nos: NC_000070.6, NT_166299.2, AC_000026.1, AAHY01041891.1, AB039044.1, AB039045.1, AB039046.1, AB039047.1, AB039048.1, AB039049.1, AB039050.1, AB039051.1, AB039052.1, AL714013.9, CH466594.1, CU210867.6, D16497.1, D82049.1, and S58667.1. Mouse Nppb mRNA sequences also include Genbank Accession Nos: AK003128.1, BC061165.1, BU609640.1, and CK128345.1. Mouse Nppb amino acid sequences include Genbank Accession Nos: BAB68568.1, BAB68569.1, BAB68570.1, BAB68571.1, BAB68572.1, BAB68573.1, BAB68574.1, BAB68575.1, BAB68576.1, EDL14790.1, BAA03948.1, BAA24159.1, AAB26344.2, BAB22588.1, and AAH61165.1. Other mouse sequences, as well as other Nppb species can be employed in accordance with the invention.

In an embodiment, the Npra sequence is a mouse sequence. For example, mouse Npra is assigned Gene NCBI Entrez Gene ID No. 18160. The mouse Npra gene is found on chromosome 3 at 3 F1. A transcript includes mRNA Genbank Accession No.: NM_008727.5 (SEQ ID NO: 9), with corresponding protein sequence NP_032753.5 (SEQ ID NO: 10). Mouse genomic Npra sequences include Genbank Accession Nos: NC_000069.6, AC_000025.1, AAHY01029027.1, AC145082.10, AJ307712.1, and CH466547.2. Mouse Npra mRNA sequences also include Genbank Accession Nos: AK135008.1, BC110659.1, BC139767.1, CJ065787.1, J05504.1, and L31932.1. Mouse Npra amino acid sequences include Genbank Accession Nos: CAC41350.1, EDL15140.1, BAE22383.1, AAI10660.1, AAA37670.1, and AAA66945.1. Other mouse sequences, as well as other Npra species can be employed in accordance with the invention. Human and mouse antisense nucleic acids are commercially available (e.g., from Ori-Gene Technologies, Inc., Rockville, Md. or Sigma-Aldrich, St. Louis, Mo.) and can be prepared using the nucleic acid sequences encoding the Nppb or Npra proteins disclosed herein and routine techniques.

In accordance with an embodiment of the invention, the Nppb blocking agent, such as an RNAi agent, such as a shMIR, can target a nucleotide sequence selected from the group consisting of the 5' untranslated region (5' UTR), the 3' untranslated region (3' UTR), and the coding sequence of Nppb or Npra, complements thereof, and any combination thereof. Any suitable Nppb or Npra target sequence can be employed. In an embodiment of the invention, the sequences of the Nppb blocking agent can be designed against a human Nppb with the sequence of Accession No. NM_002521.2 (SEQ ID NO: 1). In an embodiment of the invention, the sequences of the Nppb blocking agent can be designed against human Npra with either one of the sequences of Accession Nos: NM_000906.3 (SEQ ID NO: 3) or NM_005245218.1 (SEQ ID NO: 5), but also recognize the other sequence. In still another embodiment, the sequences of the Nppb blocking agent can be designed against a mouse Nppb with the sequence of Accession No. NM_008726.4 (SEQ ID NO: 7) or a mouse Npra with the sequence of Accession No. NM_008727.5 (SEQ ID NO: 9). RNAi agents can be designed against any appropriate Nppb or Npra mRNA sequence.

In another embodiment, the Nppb blocking agent is an Nppb receptor/Fc fusion protein. The Nppb receptor/Fc fusion protein is a soluble variation of the native Npra which binds Nppb protein, thereby competing with the native, cell surface Npra for binding to Nppb. Accordingly, the Nppb receptor/Fc fusion protein may inhibit the binding of Nppb to the native Npra. The Nppb receptor/Fc fusion protein may also inhibit the activation of any one or more of various downstream targets of Nppb signaling (e.g., GRP). The Nppb receptor/Fc fusion protein may be from any mammal. In a preferred embodiment, the Nppb receptor/Fc fusion protein is a mouse Nppb receptor/Fc fusion protein or a human Nppb receptor/Fc fusion protein.

The Nppb blocking agent can be obtained by methods known in the art. For example, Nppb blocking agents that are peptides or polypeptides can be obtained by de novo synthesis as described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; and U.S. Pat. No. 5,449,752. Also, Nppb blocking agents can be recombinantly produced using standard recombinant methods. See, for instance, Sambrook et al., *Molecular Cloning: A Laboratory Manual*, 4th ed., Cold Spring Harbor Press, Cold Spring Harbor, N.Y. 2012. Further, the Nppb blocking agent can be isolated and/or purified from a natural source, e.g., a human. Methods of isolation and purification are well-known in the art. In this respect, the Nppb blocking agents may be exogenous and can be synthetic, recombinant, or of natural origin.

The Nppb blocking agents that are peptides or polypeptides can be glycosylated, amidated, carboxylated, phosphorylated, esterified, N-acylated, cyclized via, e.g., a disulfide bridge, or converted into an acid addition salt and/or optionally dimerized or polymerized, or conjugated. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Of course, the method of the invention can comprise administering two or more Nppb blocking agents, any of which may be the same or different from one another. Furthermore, the Nppb blocking agent can be provided as part of a larger polypeptide construct. For instance, the Nppb blocking agent can be provided as a fusion protein comprising an Nppb blocking agent along with other amino acid sequences or a nucleic acid encoding same. The Nppb blocking agent also can be provided as part of a conjugate or nucleic acid encoding same. Conjugates, as well as methods of synthesizing conjugates in general, are known in the art (See, for instance, Hudecz, F., Methods *Mol. Biol.* 298: 209-223 (2005) and Kirin et al., Inorg. Chem. 44(15): 5405-5415 (2005)).

In an embodiment of the invention, the Nppb blocking agent is not neurotoxic. In this regard, the Nppb blocking agent blocks the biological activity of Nppb without ablating cells. In an embodiment, the Nppb blocking agent is not a Nppb-saporin conjugate. Accordingly, an embodiment of the invention provides a method of treating, reducing, or preventing pruritis in a mammal, the method comprising administering at least one natriuretic polypeptide b (Nppb) blocking agent to the mammal in an amount effective to treat, reduce, or prevent pruritis in the mammal, wherein the Nppb blocking agent is not a Nppb-saporin conjugate.

The Nppb blocking agent can be administered to the mammal by administering a nucleic acid encoding the Nppb blocking agent to the mammal. "Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide.

Nucleic acids encoding the Nppb blocking agent (and degenerate nucleic acid sequences encoding the same amino acid sequences), can be constructed based on chemical synthesis and/or enzymatic ligation reactions using procedures known in the art. See, for example, Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides).

The nucleic acids can be incorporated into a recombinant expression vector. For purposes herein, the term "recombinant expression vector" means a genetically-modified oligonucleotide or polynucleotide construct that permits the expression of an mRNA or polypeptide by a host cell, when the construct comprises a nucleotide sequence encoding the mRNA or polypeptide, and the vector is contacted with the cell under conditions sufficient to have the mRNA or polypeptide expressed within the cell. The vectors are not naturally-occurring as a whole. However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages does not hinder the transcription or replication of the vector.

The recombinant expression vector can be any suitable recombinant expression vector, and can be used to transform or transfect any suitable host. Suitable vectors include those designed for propagation and expansion or for expression or both, such as plasmids and viruses. The vector can be of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors can be prepared using standard recombinant DNA techniques described in, for example, Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide protophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter and/or stop codon operably linked to the nucleotide sequence encoding the Nppb blocking agent, or to the nucleotide sequence which is complementary to the nucleotide sequence encoding the Nppb blocking agent. The selection of stop codons and promoters, e.g., strong, weak, inducible, tissue-specific and developmental-specific, is within the ordinary skill of the artisan. Similarly, the combining of a nucleotide sequence with a stop codon and a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The Nppb blocking agent and nucleic acids encoding them can be of synthetic or natural origin, and can be isolated or purified to any degree. The terms "isolated" and "purified" as used herein means having been increased in purity, wherein "purity" is a relative term, and not to be necessarily construed as absolute purity. For example, the purity can be at least about 50%, can be greater than about 60%, about 70% or about 80%, or can be about 100%.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of pruritis in a mammal. Furthermore, the treatment or prevention provided by the inventive method can include treatment or prevention of one or more conditions or symptoms of the pruritis, e.g., chronic pruritis, being treated or prevented. Also, for purposes herein, "prevention" can encompass delaying the onset of the pruritis, or a symptom or condition thereof. With respect to the inventive methods, the pruritis can be any pruritis, including any of the types of pruritis caused by or associated with any of the conditions or treatments discussed herein.

For purposes of the invention, the amount or dose of the Nppb blocking agent administered should be sufficient to effect the desired biological response, e.g., a therapeutic or prophylactic response, in the mammal over a reasonable time frame. The dose will be determined by the efficacy of the particular Nppb blocking agent and the condition of the mammal (e.g., human), as well as the body weight of the mammal (e.g., human) to be treated. The dose of the Nppb blocking agent also will be determined by the existence, nature and extent of any adverse side effects that might accompany the administration of a particular Nppb blocking agent. Typically, the attending physician will decide the dosage of the Nppb blocking agent with which to treat each individual patient, taking into consideration a variety of factors, such as age, body weight, general health, diet, sex, Nppb blocking agent to be administered, route of administration, and the severity of the condition being treated.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. The mammal can be non-diseased, a mammal afflicted with pruritis, or a mammal predisposed to pruritis.

Administering an Nppb blocking agent to the mammal in accordance with the inventive methods may comprise administering a pharmaceutical composition comprising the Nppb blocking agent and a pharmaceutically acceptable carrier. The carrier can be any of those conventionally used and is limited only by chemico-physical considerations, such as solubility and lack of reactivity with the active compound(s), and by the route of administration. The pharmaceutically acceptable carriers described herein, for example, vehicles, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use. The choice of carrier will be determined in part by the particular compounds used in the pharmaceutical composition, as well as by the particular method used to administer the Nppb blocking agent.

In an embodiment of the invention, administering the Nppb blocking agent to the mammal may comprise administering the Nppb blocking agent orally, intravenously, intramuscularly, subcutaneously, or intraperitoneally. The following formulations for oral, intravenous, intramuscular, subcutaneous, or intraperitoneal administration are exemplary and are in no way limiting. More than one route can be used to administer the Nppb blocking agent, and in certain instances, a particular route can provide a more immediate and more effective response than another route.

Oral formulations may include any suitable carrier. For example, formulations suitable for oral administration may comprise suitable carriers, such as lactose, sucrose, starch, talc magnesium stearate, crystalline cellulose, methyl cellulose, carboxymethyl cellulose, glycerin, sodium alginate or gum arabic among others.

Intravenous, intramuscular, subcutaneous, or intraperitoneal formulations may include any suitable carrier. For example, formulations suitable for intravenous, intramuscular, subcutaneous, or intraperitoneal administration may comprise sterile aqueous solutions of the Nppb blocking agent with solutions which are preferably isotonic with the blood of the recipient. Such formulations may be prepared by dissolving the Nppb blocking agent in water containing physiologically compatible substances such as sodium chloride (e.g. 0.1-2.0M), glycine, and the like, and having a buffered pH compatible with physiological conditions to produce an aqueous solution, and rendering said solution sterile.

An embodiment of the invention provides an in vitro method of identifying a compound that inhibits Nppb activity, the method comprising: (a) transducing one or more tester cells and one or more control cells with at least one nucleotide sequence encoding a constitutive reporter gene and Npra comprising a nucleotide cyclase domain, wherein the nucleotide cyclase domain converts adenosine triphosphate (ATP) to cyclic adenosine monophosphate (cAMP) and the constitutive reporter gene is under the transcriptional control of cyclic adenosine monophosphate (cAMP); (b) contacting the tester cells of a) with a test agent and Nppb; (c) contacting the control cells of (a) with Nppb; (d) incubating the cells; and (e) measuring the amount of reporter gene expression in the cells of (b) and (c), wherein a reduction in reporter gene expression in the cells of (b) as compared to the reporter gene expression in the cells of (c) is indicative of a compound that inhibits Nppb activity. In an embodiment, the method is a high-throughput method of identifying a compound that inhibits Nppb activity.

The tester cells and control cells may be any suitable cell line. The method may comprise transducing the tester cells and control cells in any suitable manner known in the art with at least one nucleotide sequence encoding a constitutive reporter gene and Npra comprising a nucleotide cyclase domain, wherein the nucleotide cyclase domain converts ATP to cAMP and the constitutive reporter gene is under the transcriptional control of cAMP.

The constitutive reporter gene may be any suitable constitutive reporter gene known in the art. Examples of constitutive reporter genes include, but are not limited to, any of fluorescent protein (e.g., green (GFP), red, yellow, or cyan fluorescent protein, enhanced green, red, yellow, or cyan fluorescent protein), beta-lactamase, beta-galactosidase, luciferase (e.g., firefly luciferase (FLuc), Renilla (RLuc) luciferase, NANOLUC luciferase (NlucP) (Promega, Madison, Wis.), bacterial luciferase, Click-Beetle Luciferase Red (CBRluc), Click-Beetle Luciferase Green (CBG68luc and CBG99luc), Metridia pacifica Luciferase (MetLuc), Gaussia Luciferase (GLuc), Cypridina Luciferase, and Gaussia-Dura Luciferase), chloramphenicol acetyltransferase (CAT), neomycin phosphotransferase, alkaline phosphatase, secreted alkaline phosphatase (SEAP), Chloramphenicol acetyltransferase (CAT), mCherry, tdTomato, TurboGFP, TurboRFP, dsRed, dsRed2, dsRed Express, AcGFP1, ZsGreen1, Red Firefly Luciferase, Enhanced Click-Beetle Luciferase (ELuc), Dinoflagellate Luciferase, Pyrophorus plagiophthalamus Luciferase (lucGR), Bacterial luciferase (Lux), pmeLUC, Phrixothrix hirtus Luciferase, Gaussia-Dura Luciferase, RenSP, Vargula hilgendorfii Luciferase, Lucia Luciferase, Metridia longa Luciferase (MetLuc), HaloTag, SNAP-tag, CLIP-tag, β-Glucuronidase, Aequorin, Secreted placental alkaline phosphatase (SPAP), Gemini, TagBFP, mTagBFP2, Azurite, EBFP2, mKalamal, Sirius, Sapphire, T-Sapphire, ECFP, Cerulean, SCFP3A, mTurquoise, mTurquoise2, Midoriishi-Cyan, TagCFP, mTFP1, Emerald, Superfolder GFP, Azami Green, TagGFP2, mUKG, mWasabi, Clover, Citrine, Venus, SYFP2, TagYFP, Kusabira-Orange, mKO, mKO2, mOrange, mOrange2, mRaspberry, mStrawberry, mTangerine, TagRFP, TagRFP-T, mApple, mRuby, mRuby2, mPlum, HcRed-Tandem, mKate2, mNeptune, NirFP, TagRFP657, IFP 1.4, iRFP, mKeima Red, LSS-mKate1, LSS-mKate2, PA-GFP, PAmCherryl, PATagRFP, Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, PSmOrange, Dronpa, TurboYFP, TurboFP602, TurboFP635, TurboFP650, hrGFP, hrGFP II, E2-Crimson, HcRedl, Dendra2, AmCyanl, ZsYellowl, mBanana, EBFP, Topaz, mECFP, CyPet, yPet, PhiYFP, DsRed-Monomer, Kusabira Orange, Kusabira Orange2, Jred, AsRed2, dKeima-Tandem, AQ143, mKikGR, and homologs and variants thereof.

The method may further comprise contacting the transduced tester cells with one or more test agents and Nppb. In an embodiment, the tester cells are contacted with a library of potential Nppb blocking agents (e.g., chemical inhibitors) and Nppb. The tester cells may be contacted with one or more test agents and Nppb in any suitable manner. In an embodiment, the method comprises physically contacting the tester cells with one or more test agents and Nppb. In an embodiment of the invention, each of multiple subpopulations of tester cells is contacted with a different test agent or combination of test agents in, for example, multiwell plates.

The method may further comprise contacting the transduced control cells with Nppb. The cells may be contacted with Nppb in any suitable manner. In an embodiment, the method comprises physically contacting the control cells with Nppb.

The method may further comprise incubating the cells. The cells may be incubated under any suitable culture conditions known in the art for the particular cells being used.

The method may further comprise measuring the amount of reporter gene expression in the contacted, transduced tester cells and the contacted, transduced control cells. The amount of reporter gene expression may be measured in any suitable manner known in the art. A reduction in reporter gene expression in the tester cells as compared to the reporter gene expression in the control cells is indicative of a compound that inhibits Nppb activity.

The following examples further illustrate the invention but, of course, should not be construed as in any way limiting its scope.

EXAMPLES

Materials and Methods

All experiments using animals followed NIH guidelines and were approved by the National Institute of Dental and Craniofacial ACUC. The targeted JM8A3 ES-cell clone A04 with disruption of the Nppb gene was obtained from Mouse Biology Program (MBP), UC Davis and was used to generate chimeric mice. Chimeras were crossed with C57BL/6 mice and heterozygous offspring were mated to generate paired knockouts and controls. Transgenic (Tg) (gastrin releasing peptide (GRP)-enhanced green fluorescent protein (EGFP)) animals (Gong et al., Nature, 425:917 (2003)) were employed to localize expression of GRP. Male C57BL/6 (8-14 weeks) mice were used for selective toxin ablation and GRP-antagonist itch experiments. Ablation of Npra and GRP-receptor-expressing spinal cord interneurons was accomplished by intrathecal (segment L3/4) injection of Nppb-saporin (5 μg in 10 μl; Advanced targeting Systems, San Diego, Calif.) and GRP-saporin (2.5 μg) respectively. Experiments were initiated two weeks after toxin injection.

Itch inducing substances (see Table 1) were injected intradermally into the shoulder of mice and numbers of scratching bouts assessed over 30 minutes. Table 1 shows a list of pruritic agents and dose injected subcutaneously.

Table 1 also indicates the receptors or mechanisms believed to be activated by the various compounds in the itch response pathway.

Pruriceptive (itch) behavior was also elicited by lumbar 4-5 segment intrathecal injection of Nppb (5 µg in 10 µg) or GRP (1 nM in 10 µl); just like responses to pruritogens, responses to peptides exhibited delayed onset of approximately (approx.) 5 minutes. Pretreatment with GRP antagonist deamino-Phe19,D-Ala24,D-Pro26-D-Phe27-GRP (Yegen et al., *Regulatory Peptides*, 61:175 (1996)) (1 nM in 10 µl) was used to block GRP-receptor.

TABLE 1

| Pruritogen | Dose (10 µl) | Receptor |
|---|---|---|
| Histamine | 100 µg | Histamine (H1) |
| Chloroquine | 100 µg | MrgprA3 |
| Endothelin (ET-1) | 25 ng | ETA |
| 2-methyl serotonin (5HT) | 30 µg | 5-HT |
| SLIGRL-NH2 (PAR2) | 100 µg | MrgprC11 |
| Compound 48/80 (48/80) | 100 µg | Mast-cells |

Thermal, mechanical, proprioceptive and pruriceptive behavioral responses were assessed as described previously (Mishra et al., *EMBO J.*, 30:582 (2011)). Thermal reactivity was determined using a hot plate (55° C.) or cold plate (−5° C.), with the time to the first lick or jump recorded. Mechanical sensitivity was measured using a semi-automated von-Frey apparatus and Randall-Sellito device. Proprioceptive responses were assessed using an accelerating rotarod. Statistical analysis used Prism Graph; $P>0.05$ values were considered non-significant.

In situ hybridization (ISH) was performed at high stringency (washed 30 minutes (min), 0.2×SSC, 70° C.) as described previously (Hoon et al., *Cell*, 96:541 (1999), Adler et al., *Cell*, 100:693 (2000)). Detection of MAS-related G-protein coupled receptor (GPR), member A (MrgprA)-receptors used a mix of full-length MAS-related GPR, member A3 (MrgprA3) and MAS-related GPR, member A4 (MrgprA4) anti-sense probes. Nppb-expression outside the somatosensory system was examined and signal was not detected in other sensory systems or the brain. As expected, Nppb was prominently expressed in the heart. Immunohistochemistry was performed with monoclonal antibody (mAb) anti-Nppb, rabbit anti-MAS-related GPR, member X1 (MrgprC11), and rabbit anti-Npra (from LifeSpan Bioscience, Seattle, Wash.); chicken anti-GFP was from Abeam (Cambridge, England) and secondary antibodies were Jackson Immunolabs (West Grove, Pa.); tyramine FITC was used for HRP-signal amplification to visualize Npra-immunostaining. Fluorescent images (1 µm optical sections) were collected using confocal microscopy and were processed using Adobe Photoshop.

Total RNA was extracted from dorsal root ganglia (DRG) and spinal cord using an RNAeasy kit and converted into cDNA. Quantitative real-time PCR was accomplished with commercially available TAQMAN primer sets. Equal amounts of cDNA were used in duplicate and amplification efficiencies were validated and normalized against glyceraldehyde 3-phosphate dehydrogenase (GAPDH), fold increases were calculated using the comparative threshold cycle method. Agilent whole genome arrays (mouse GE 44K V2) were screened with cRNA probes generated from DRG as recommended by the manufacturer. Bioinformatic analysis was performed with Gene-Spring software.

Example 1

This example demonstrates that Nppb is co-expressed with itch related signaling molecules TRPV1 and PLCβ3.

Mice were previously generated that had lost all transient receptor potential cation channel, subfamily V, member 1 (TRPV1)-lineage neurons (Mishra et al., *EMBO J.*, 30:582 (2011)). TRPV1-DTA mice exhibited dramatically reduced scratch responses following intradeimal injection of pruritic agents histamine (100 µg in 10 µl); chloroquine (100 µg); endothelin 1 (1 µM); methyl-serotonin (30 µg); PAR2 agonist SLIGRL-NH2 (100 µg) and compound 48/80 (100 µg). Itch-inducing substances were injected intradermally into the shoulder of mice and numbers of scratching bouts were assessed over 30 minutes. As shown in FIG. 1A, these mice had major pruritic deficits as well as a complete loss of thermosensory input (Mishra et al., *EMBO J.*, 30:582 (2011)), in keeping with previous reports using capsaicin-induced lesions (Imamachi et al., *PNAS*, 106:11330 (2009), Cavanaugh et al., *PNAS*, 106:9075 (2009)).

To identify candidate molecules that might mediate itch signaling, a differential microarray-based screen that identified many TRPV1-enriched transcripts (Table 2) was used. Table 2 shows the top 25 over-expressed genes in wild-type versus (vs) TRPV1-DTA mice. In situ hybridization (ISH) of sections through the DRG showed the loss of Nppb-expression in TRPV1-DTA animals. Quantitation of Nppb expressing neurons revealed that 7±0.6% of NeuN-positive C4 DRG neurons expressed the neuropeptide in wild type mice (n=6). Amongst the genes in Table 2, the natriuretic polypeptide b (Nppb) was prominently expressed in a small subset of DRG neurons, but was dramatically decreased in sensory ganglia from TRPV1-DTA animals.

TABLE 2

| Gene name | Fold-change | P-value | Genbank acc # |
|---|---|---|---|
| Apod | 105 | 3.8e−5 | NM_007470 |
| Trpv1 | 96 | 1.3e−4 | NM_001001445 |
| Myot | 32 | 8.7e−6 | NM_001033621 |
| Zcwpw2 | 32 | 7.5e−2 | XM_001473321 |
| Gfra3 | 32 | 2.1e−6 | NM_010280 |
| Tnnt3 | 28 | 1.9e−6 | NM_001163664 |
| Osta | 27 | 2.4e−5 | NM_145932 |
| Myl1 | 27 | 2.1e−4 | NM_001113387 |
| Ceacam10 | 26 | 1.4e−4 | NM_007675 |
| Wfdc2 | 26 | 2.8e−5 | NM_026323 |
| Kcnf1 | 25 | 6.2e−4 | NM_201531 |
| Trdn | 25 | 4.3e−5 | NM_001251987 |
| Nppb | 25 | 2.2e−6 | NM_008726 |
| Cacna2 | 25 | 9.7e−5 | NM_001110843 |
| Dgkk | 25 | 2.1e−4 | NM_177914 |
| AW551984 | 25 | 1.0e−3 | NM_001199556 |
| Syt16 | 21 | 4.4e−5 | NM_172804 |
| Cacna1i | 21 | 6.7e−6 | NM_001044308 |
| Gpr35 | 21 | 3.2e−4 | NM_022320 |
| 9430021M05Rik | 21 | 3.9e−5 | NR_033569 |
| Tnnc2 | 21 | 2.1e−6 | NM_009394 |
| Avpr1a | 20 | 8.9e−4 | NM_016847 |
| Bex1 | 19 | 3.6e−6 | NM_009052 |
| Trpa1 | 19 | 8.1e−7 | NM_177781 |
| P2rx3 | 18 | 1.6e−6 | NM_145526 |

Double label ISH of DRG demonstrated that Nppb and TRPV1 were co-expressed in the same sensory neurons. Only a subset of TRPV1 expressing neurons contained Nppb. All Nppb-positive neurons also expressed PLCβ3 but many PLCβ3 neurons were Nppb negative. Accordingly, double label ISH demonstrated that all Nppb-expressing neurons contained TRPV1 and PLCβ3, which are critically required for histamine-induced scratching in mice (Imamachi et al., *PNAS*, 106:11330 (2009), Han et al., *Neuron*, 52:691 (2006)).

Double-label ISH also showed that Nppb-positive neurons all expressed MrgprA receptors (including MrgprA3, the receptor for chloroquine), with more than 70% of MrgprA expressing-neurons also containing the neuropeptide. Double-label immunostaining demonstrated complete overlap between expression of MrgprC11, the receptor for the pruritogen SLIGL-NH$_2$ and Nppb in somatosensory neurons. Accordingly, double labeling showed almost complete overlap between the expression of Nppb and two Mas related G protein coupled receptors that have recently been shown to detect specific pruritogens (Liu et al., *Cell*, 139: 1373 (2009), Liu et al., *Science Signaling*, 4:ra45 (2011), Han et al., *Nat. Neurosci.*, 16:174 (2012)).

Many itch-inducing agents also trigger a peripheral inflammatory response. Therefore, double label in situ hybridization was used to determine whether Nppb-expressing neurons in DRG also contain neuropeptides that are known to be released in the periphery and cause neurogenic inflammation. Very few Nppb-positive cells co-expressed substance P (Sub P). However, about a quarter of Nppb-expressing neurons contained CGRP and half of the Nppb-neurons expressed neuromedin B (NMB). Quantification of the Nppb positive neurons revealed that 2% co-labeled for Substance P, 24%, for CGRP and 50% for NMB (assessed from total neuronal counts of 147, 185, and 196 respectively).

Example 2

This example demonstrates the generation and characterization of Nppb$^{-/-}$ mice.

Nppb$^{-/-}$ animals were generated by inserting a splice acceptor-lacZ cassette into the second Nppb exon, as shown in FIG. 1B. In situ hybridization of sections through DRG revealed that Nppb expression was lost in Nppb$^{-/-}$ animals, showing that these mutants displayed no detectable expression of Nppb.

The mice were healthy and had normal numbers of nociceptive, touch, and proprioceptive neurons. The distribution and number of dorsal horn interneurons were unaffected by gene disruption. Sections through DRG and spinal cord from wild-type control and Nppb$^{-/-}$ mice were hybridized with probes for Nppb and for genes expressing molecules involved in pruriception, nociception, proprioception, mechanical, and thermal sensation (TRPV1, TRPA1, TRPM8, Mrgc11, tyrosine hydroxylase (TH), TrkB, TrkC, Npy2r, MrgD, Sst, Tac1, Npy, Gal, and Npra). Except for Nppb, no significant changes between genotypes were observed in numbers of positive cells.

Nppb$^{-/-}$ mice retained normal responses to thermal, nocieptive, touch, and proprioceptive stimulation when tested using standard assays (FIG. 1C).

Intradermal injections were performed. The number of scratching bouts for substances that directly activate pruriceptors was recorded. The number of scratching bouts after injection with compound 48/80, which causes itch via an indirect route (McNeil et al., *Neuroscience Bulletin*, 28:100 (2012)), was also recorded. All of these agents (Table 1) reliably triggered multiple bouts of scratching in control animals (FIG. 1D), but Nppb$^{-/-}$ mice were almost completely insensitive to the full range of pruritic substances tested (FIG. 1D).

How Nppb induces this stereotyped scratch response was investigated. It was hypothesized that because this peptide is prominently expressed in somatosensory neurons, the most plausible explanation for its role would be if it acted as a specific itch-related neuromodulator (or neurotransmitter) in the spinal cord. Intrathecal injection of Nppb (5 µg in 10 µl) into the lumbar 4-5 segment of control and Nppb$^{-/-}$ mice induced repeated bouts of scratching (FIG. 1E). Injection of GRP (1 nM in 10 µl) also triggered itch responses in both mutant and control animals (FIG. 1E). Indeed, intrathecal injection of Nppb induced profound scratching behavior in wild type animals (FIG. 1E), demonstrating that spinal-Nppb is sufficient to induce itch even without activation of the peripheral neurons that express it. Intrathecal injection of Nppb into Nppb$^{-/-}$ mice also led to an equivalent phenotype (FIG. 1E). No significant differences in response between genotypes were found (Student's t-test). Loss of Nppb in sensory afferents was thus responsible for the pruriceptive deficits seen in mutant mice. Without being bound to a particular theory or mechanism, it is believed that Nppb-expression delineates the subset of somatosensory neurons that detect pruritic agents and that central release of Nppb from these neurons is necessary for the itch response.

Example 3

This example demonstrates that selective ablation of Npra receptor neurons in the spinal cord impairs pruriception.

Because Nppb is responsible for transmitting the peripheral signals that trigger pruritic responses, its receptor Npra (Misono et al., *The FEBS Journal*, 278:1818 (2011)) should be expressed at the site of afferent fiber synaptic connections in the spinal dorsal horn and mark the secondary neurons in the itch response circuit. Therefore, expression of Npra in the dorsal spinal cord was assessed using ISH. In normal mice, a significant subset of interneurons in the outer layer express Npra, however after intrathecal administration of Nppb-saporin, few Npra neurons remained. In contrast, the number of GRP-receptor positive cells were unaffected by Nppb-saporin. Therefore, it was found that Npra was, indeed, expressed in a limited subset of neurons (most likely interneurons, see below), primarily in the outer layer, i.e., lamina I, corresponding to the terminal field of TRPV1-expressing sensory neurons (Caterina et al., *Science*, 288: 306 (2000)).

To examine whether the Npra neurons in the spinal cord function in the itch circuit and if they are selectively required for pruritogen-induced scratching (rather than other somatosensory responses), a targeted-toxin cell ablation strategy was used (Wiley et al., *Advanced Drug Delivery Reviews*, 55:1043 (2003)). An Nppb-saporin conjugate was injected intrathecally into wild type mice to target their Npra-expressing cells, and the effectiveness, specificity and behavioral consequences of administering this toxin were assessed. ISH analysis of Nppb-saporin treated mice and untreated mice showed that intrathecal Nppb-saporin treatment had no effect on expression patterns of spinal cord neuropeptides Sst, Tac1, Npy, or Gal. Analysis of numbers of neurons ablated by Nppb-saporin (FIG. 2A) and GRP-saporin (FIG. 2B) administration showed that approximately 70% of Npra-positive cells were eliminated by Nppb-saporin administration. By contrast, Nppb-saporin injection did not alter numbers of GRP-receptor positive neurons. ISH was performed on tissue from at least 4 control and 4 treated mice. Serial sections from >10 sections per mouse were hybridized and numbers of cells counted. Accordingly, this targeted ablation of Npra receptor neurons was highly selective, with neither cells expressing the GRP-receptor nor other dorsal horn interneurons affected by Nppb-saporin treatment.

Figure 2:
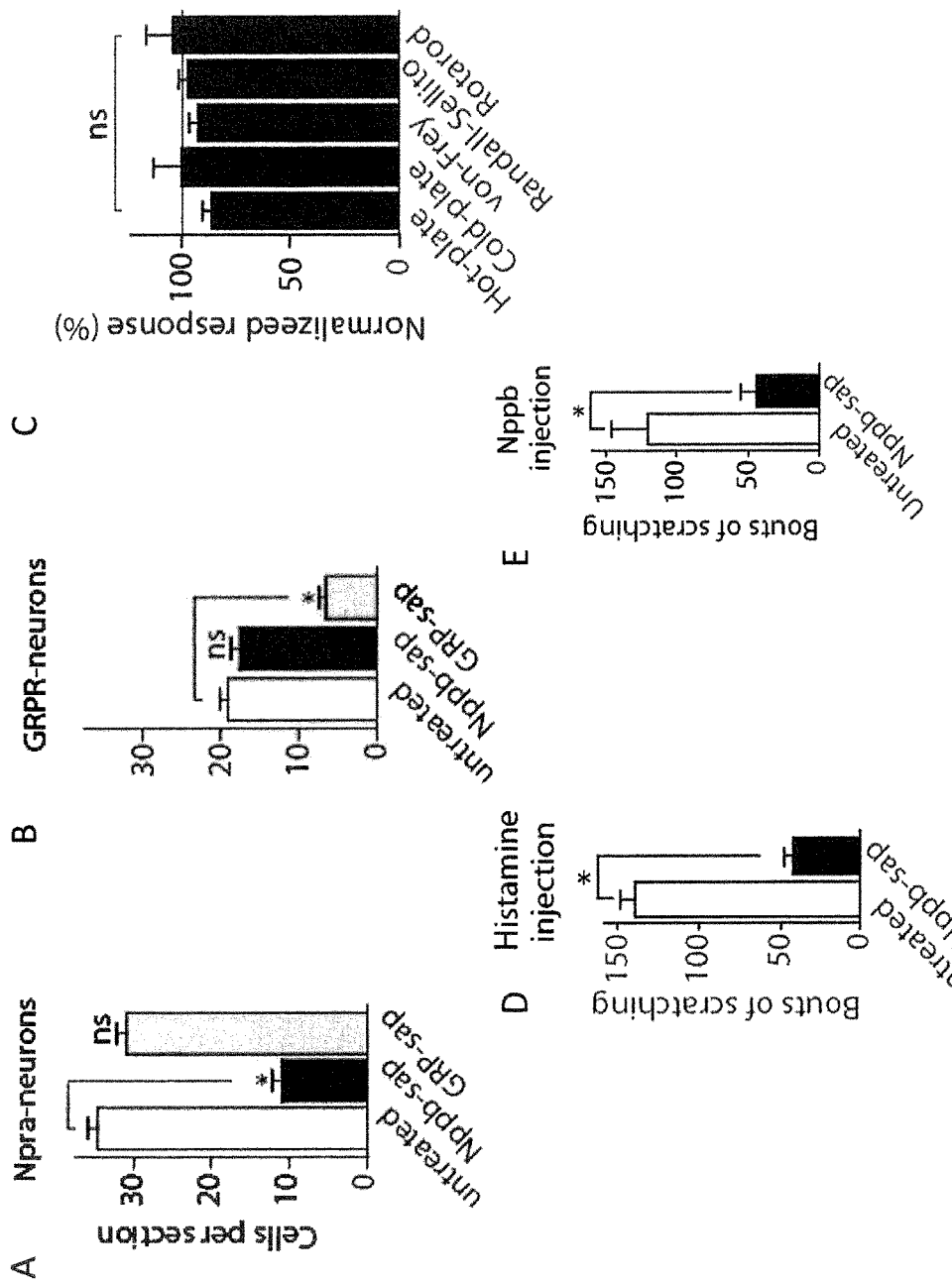
FIGS. 2A and 2B are graphs showing the number of Npra-expressing neurons (A) and GRPR-expressing neurons (B) per section in untreated mice or mice treated with Nppb-saporin or GRP-saporin. Data are mean±s.e.m. Significant differences between treatment groups were determined using Student's t-test with*indicating P<0.0001.
FIG. 2C is a graph showing the normalized response (%) of Nppb-saporin treated mice to thermal, nociceptive, touch, and proprioceptive stimulation in standard assays. Data represent means normalized against untreated controls±s.e.m. (n≥5 animals).
FIGS. 2D and 2E are graphs showing numbers of bouts of scratching after histamine (D) or Nppb (E) injection in untreated and Nppb-saporin treated mice. Data represent means normalized against untreated controls±s.e.m. (n≥5 animals). Significant differences between genotypes were determined using Student's t-test with*indicating P<0.01.

Toxin-injected mice displayed normal responses to thermal, touch, and painful stimulation (FIG. 2C). However, a dramatic reduction in scratching evoked by histamine or Nppb (FIGS. 2D and 2E) was observed, indicating that these neurons are required for itch responses, but not for other somatosensory pathways.

Example 4

This example demonstrates that GRP acts downstream of Nppb in the rodent pruriceptive circuit.

Figure 3:
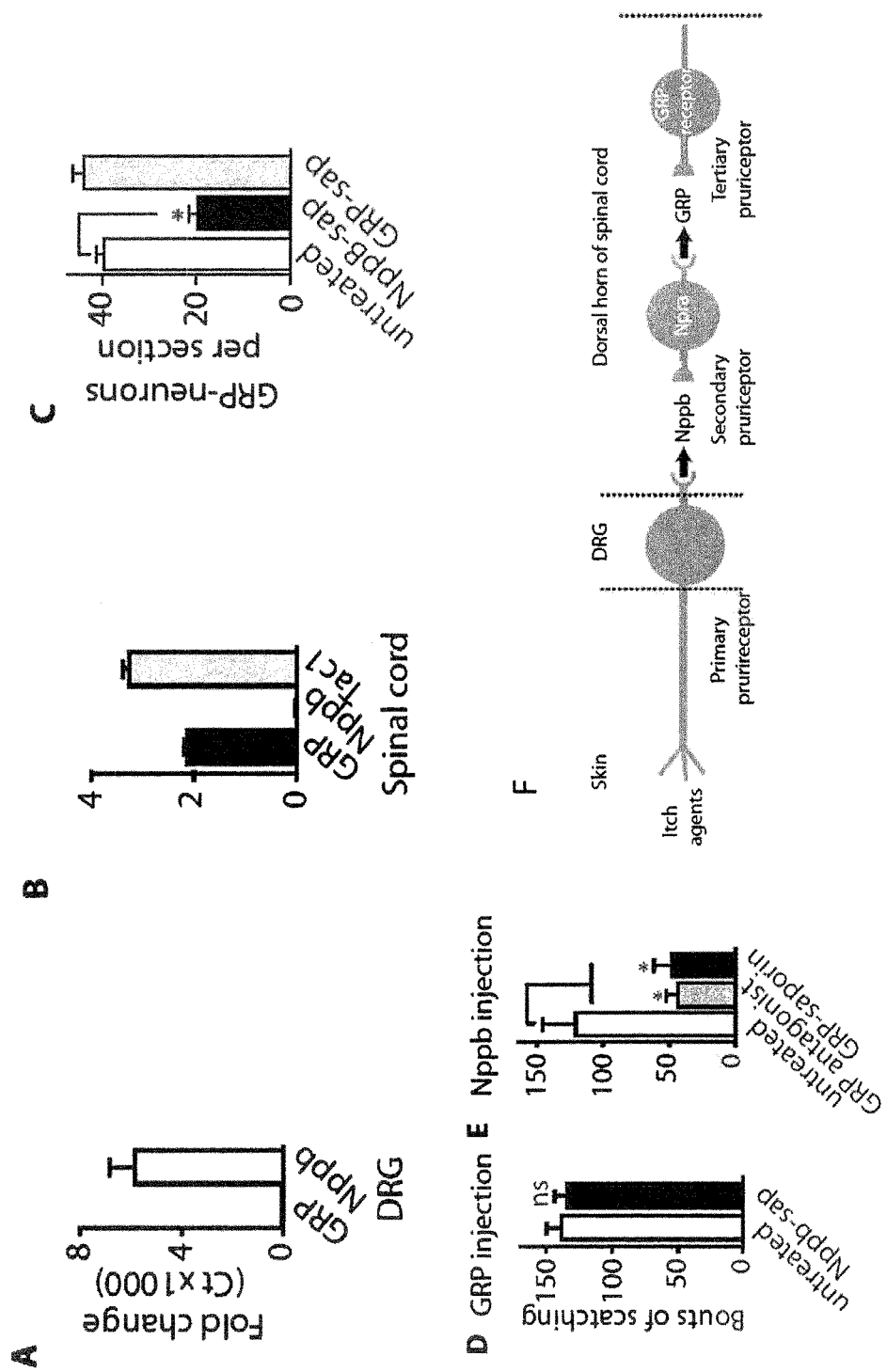
FIGS. 3A and 3B are graphs showing fold change of expression of GRP and Nppb in the dorsal root ganglia (DRG) (A) and spinal cord (B). Data represent mean±s.e.m for triplicate cDNA preparations each analyzed in two separate polymerase chain reaction (PCR) reactions. Transcript levels in DRG for GRP and Nppb were statistically different from each other (Student's t-test, P<0.001) (FIG. 3A). Transcript levels in dorsal horn (DH) of spinal cord for GRP and Tac1 were both statistically different from the amount of Nppb (Student's t-test, P<0.001) (FIG. 3B).
FIG. 3C is a graph showing the number of GRP neurons per section in untreated mice and those treated with Nppb-saporin or GRP-saporin. Data represent mean±s.e.m. (n≥4 animals). Significant differences between groups were determined using Student's t-test with*indicating P<0.001.
FIG. 3D is a graph showing numbers of bouts of scratching in untreated mice and mice treated with Nppb-saporin after injection with GRP. Data are mean±s.e.m. (n≥6 animals) and *indicates P<0.001 (Student's t-test).
FIG. 3E is a graph showing numbers of bouts of scratching in untreated mice and those treated with GRP antagonist or GRP-saporin after injection with Nppb. Data are mean±s.e.m. (n≥6 animals) and *indicates P<0.001 (Student's t-test).
FIG. 3F is a schematic model of the first three stages of the pruriceptive circuit with the neuropeptide used at each stage indicated.

The GRP-receptor has been shown to be a key element in the pruritic pathway (Sun et al., *Nature*, 448:700 (2007), Sun et al., *Science*, 325:1531 (2009)) with the suggestion that GRP might be the primary neurotransmitter for itch. However, this view has also been questioned (McNeil et al., *Neuroscience Bulletin*, 28:100 (2012), Fleming et al., *Mol. Pain*, 8:52 (2012)). Quantitative PCR (qPCR) was used to quantitate expression of GRP and Nppb relative to GAPDH in the DRG and spinal cord. GRP was robustly expressed in the spinal cord (at a level comparable with Tac1) but was almost undetectable in the DRG (FIGS. 3A and 3B). Nppb was prominently expressed in DRG, but was not present in the spinal cord (FIGS. 3A and 3B). No more than trace quantities of GRP expression were detected in the DRG using a sensitive qPCR assay (FIG. 3A).

Similarly, somatosensory neurons from GRP-reporter mice Tg(GRP-EGFP) were negative for EGFP expression. ISH and immunohistochemistry (IHC) of tissue from Tg(GRP-EGFP) animals showed that GRP was expressed in a population of dorsal horn interneurons. In contrast, GRP was not expressed by primary sensory neurons. As shown in FIG. 3C, a significant number of GRP-neurons was eliminated following Nppb-saporin (Nppb-sap) treatment. GRP-saporin (GRP-sap), which targets GRP-receptor neurons, had no effect on the number of GRP-interneurons. ISH revealed that Nppb was expressed in DRG and was absent from the spinal cord. Therefore, it was concluded that GRP cannot act at the level of pruriception, but must function downstream of Nppb. Three complementary functional strategies were applied to substantiate this hypothesis and dissect the itch response circuit.

Figure 4:
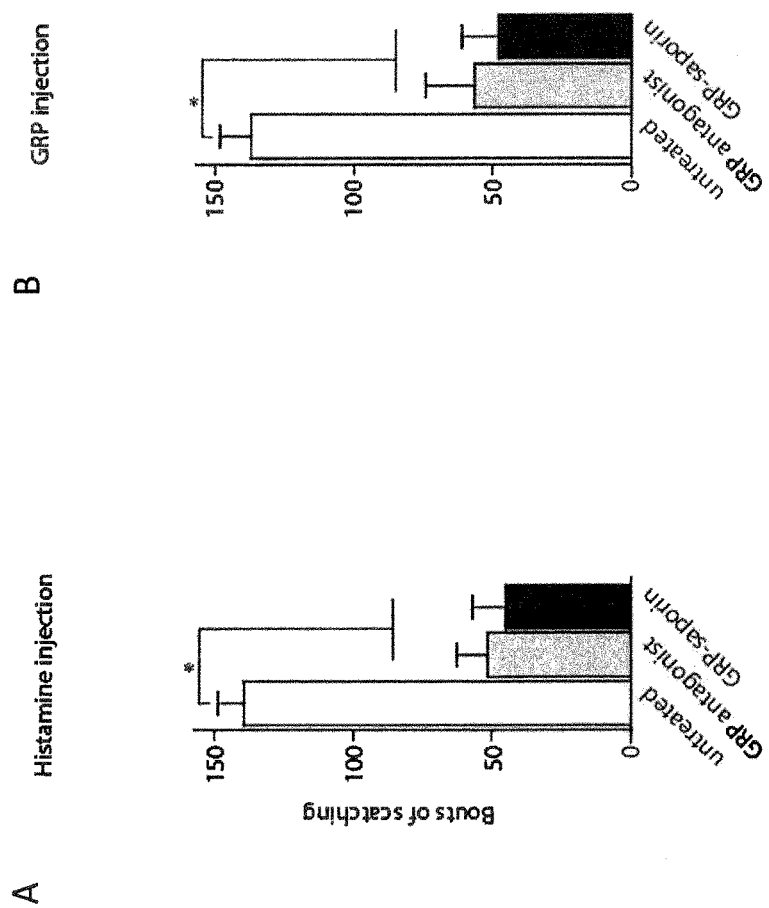
FIGS. 4A and 4B are graphs showing numbers of bouts of scratching after histamine (A) or GRP (B) injection in untreated mice or mice treated with GRP antagonist or GRP-saporin. Data represent mean±s.e.m. (n≥5 animals). Significant differences between treatment groups were determined using Student's t-test with *indicating P<0.001.

First, it was demonstrated that GRP-induced scratching was unaltered either by Nppb-knockout (FIG. 1E) or by the ablation of Npra-expressing neurons (FIG. 3D). Second, pharmacological inhibition of the GRP-receptor not only attenuated behavioral responses to the pruritic agent histamine or GRP injection (FIGS. 4A and 4B), but also inhibited scratching after intrathecal administration of Nppb (FIG. 3E). Pretreatment with a GRP antagonist or ablation of GRP-receptor expressing neurons with GRP-saporin attenuated scratching following intradermal injection of histamine or intrathecal administration of GRP (FIGS. 4A and 4B). Knockout of the GRP-receptor had a much less severe effect on behavioral-responses to histamine than pharmacological inhibition, suggesting that compensatory mechanisms may occur in GRP-R$^{-/-}$ animals. These results show that killing the GRP-R expressing cells with GRP-saporin (Sun et al., *Science*, 325:1531 (2009)) more closely resembles pharmacological inhibition of the receptor. Lastly, mice were tested with selective ablation of GRP-receptor-expressing neurons and again found significantly reduced itch responses to Nppb (FIG. 3E). As shown in FIG. 3E, scratching induced by lumbar injection of Nppb was strongly attenuated by pretreatment with a selective GRP antagonist or by the ablation of GRPR-expressing neurons with GRP-saporin.

These data place GRP downstream of Nppb in the itch response circuit. These data suggest that the secondary pruriceptors are targets for one neuropeptide, Nppb, and, in turn, signal through a second peptide, GRP. Indeed, just as this model predicts, all Npra-expressing neurons in the dorsal horn contained GRP, and Nppb-saporin treatment significantly reduced the number of GRP-expressing cells. ISH was used to analyze GRP expression in the dorsal horn of normal and Nppb-saporin treated mice. Many GRP expressing interneurons were lost on ablation of Npra-expressing cells. Double-label immunohistochemistry was used to localize interneurons expressing Npra and GRP-driven EGFP in sections through the dorsal horn of Tg(GRP-EGFP) mice.

These results molecularly characterized the first three stations of an itch response pathway in mice (FIG. 3F), demonstrated that Nppb marks the primary sensory neurons and showed that this peptide is both necessary and sufficient for transmission of peripheral signals that induce stereotypic itch responses. Unlike previously characterized receptors (Liu et al., *Cell*, 139:1373 (2009), Liu et al., *Science Signaling*, 4:ra45 (2011)) and signaling molecules (Shim et al., *J. Neurosci.*, 27:2331 (2007), Imamachi et al., *PNAS*, 106:11330 (2009), Han et al., *Neuron*, 52:691 (2006)) that affect the detection of particular itch-inducing agents, Nppb is necessary for responses to a wide range of pruritogens (i.e., compounds classed as inducing histamine and non-histamine related itch, Table 1). These data also refine the role GRP and GRP-receptor cells play in the itch response pathway by placing them at later stages than had been hypothesized previously (Sun et al., *Nature*, 448:700 (2007), Sun et al., *Science*, 325:1531 (2009)).

Example 5

This example demonstrates that an Npra antagonist, anantin, attenuates histamine-induced itch.

Figure 5:
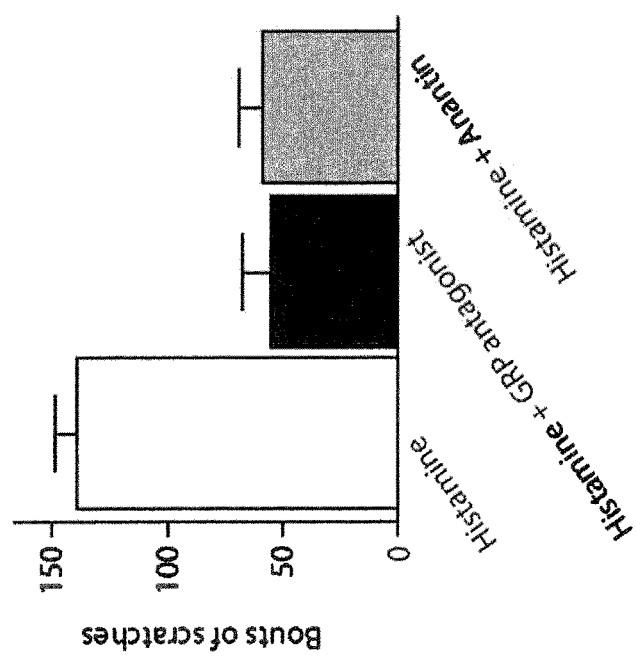
FIG. 5 is a graph showing numbers of bouts of scratches in mice that were treated with histamine alone, a combination of histamine and GRP antagonist, or a combination of histamine and anantin. Behavioral responses to histamine were statistically different from responses to histamine in the presence of either GRP-antagonist or Anantin (Student's t-test, P<0.01; n=5 mice).

Wild-type mice (C57BL/6) were administered histamine alone, a combination of histamine and a GRP antagonist, or a combination of histamine and anantin. GRP is an antagonist to another receptor in the itch pathway and was used as a control. Bouts of scratching were counted. The results are shown in FIG. 5. As shown in FIG. 5, anantin attenuated histamine-induced itch.

Example 6

This example demonstrates that elevated blood Nppb can directly produce itch in a mouse model.

Figure 6:
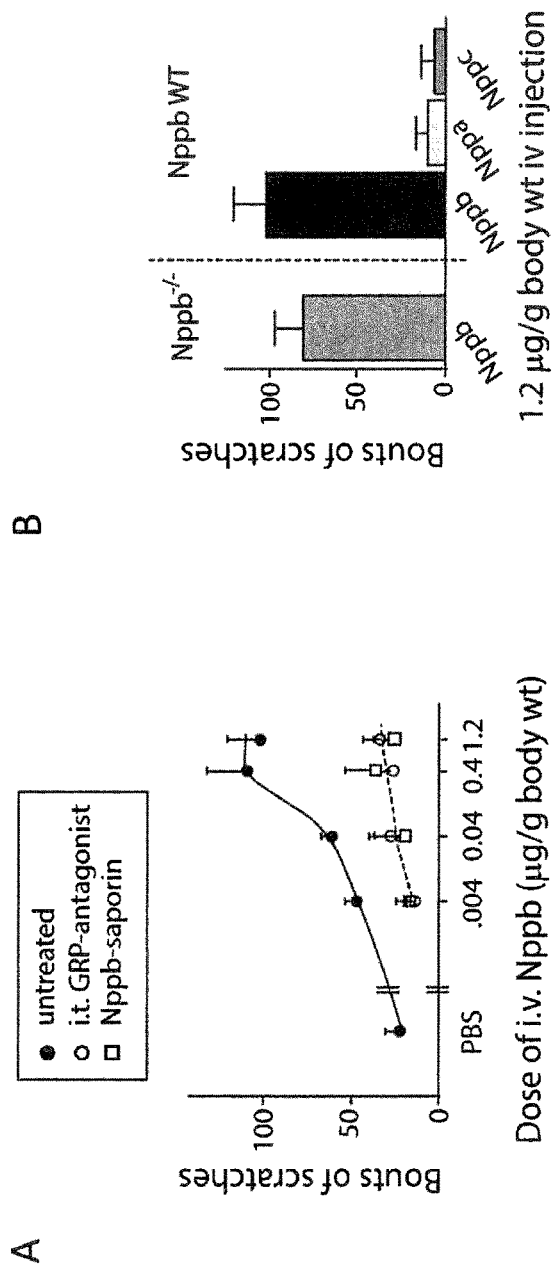
FIG. 6A is a graph showing the numbers of bouts of scratches in mice that were intravenously (i.v.) administered PBS or various doses of Nppb and untreated (shaded circles) or treated with GRP-antagonist (open circles) or Nppb-saporin (squares). Behavioral responses elicited by i.v. injection of Nppb were statistically different from those of animals pretreated either with GRP-antagonist or Nppb-saporin (Student's t-test, P<0.05; n≥5 mice).
FIG. 6B is a graph showing the numbers of bouts of scratches in Nppb-deficient or wild-type mice that were i.v. administered Nppb, natriuretic peptide A (Nppa), or natriuretic peptide C (Nppc). Behavioral responses elicited by i.v. injection of Nppb were statistically different from those induced by administration of Nppa and Nppc (Student's t-test, P<0.01; n=4-5 mice). The difference in responses to i.v. injected Nppb between Nppb knockout mice and wild-type controls was not statistically significant (Student's t-test, P>0.05; n=4-5 mice).

Elevated blood Nppb is found in kidney dialysis patients. Accordingly, the effect of elevated blood Nppb on itching in mice was evaluated. Wild-type mice (C57BL/6) were intravenously administered Nppb and were untreated or treated with GRP-antagonist or Nppb saporin. The bouts of scratching were counted. The results are shown in FIG. 6A. As shown in FIG. 6A, the i.v. Nppb-induced itch was blocked with a GRP antagonist or by eliminating neurons that express the Npra receptor (Npra is the Nppb receptor) with Nppb-saporin toxin conjugate.

Nppb deficient or wild-type (C57BL/6) mice were intravenously (i.v.) administered Nppb, Nppa, or Nppc, and the bouts of scratches were measured. The results are shown in FIG. 6B. As shown in FIG. 6B, in mouse, the elevated Nppb treatment was specific for the Nppb peptide because Nppa and Nppc did not induce significant itch. In addition, FIG. 6B shows that in a mouse deficient for Nppb, i.v. injection of itch still produced scratch responses, establishing that the Nppb acts on the central (CNS) pathway.

Example 7

This example demonstrates that itching induced by the itch-inducing agent interleukin (IL)-31 also depends on Nppb signaling.

Figure 7:
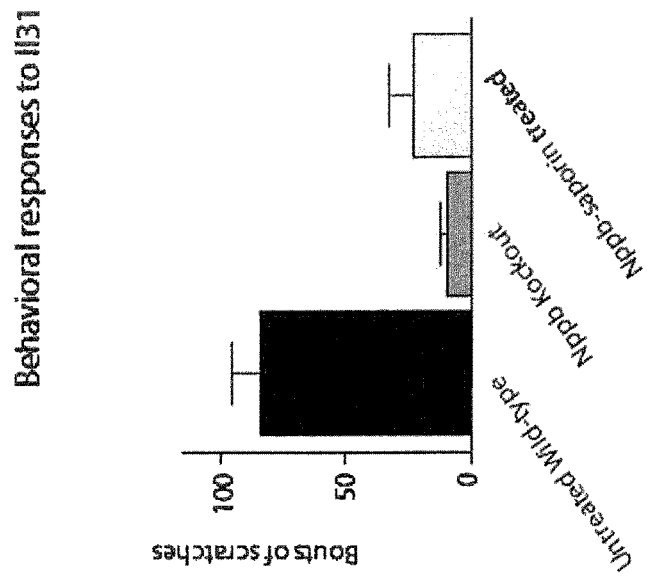
FIG. 7 is a graph showing the numbers of bouts of scratches in wild-type, Nppb knockout, or Nppb-saporin-treated mice treated with IL-31. Behavioral responses of wild-type mice to IL-31 mice were statistically different from those in wild-type control animals pretreated with Nppb-saporin and to responses observed for Nppb knockout mice (Student's t-test, P<0.005; n=5 mice).

IL-31 is a cytokine that has been linked with skin conditions and is associated with chronic itch in some types of skin disorders such as, for example, atopic dermatitis. To investigate the role of Nppb in IL-31-induced itching, wild-type (C57BL/6) (untreated with Nppb-saporin), Nppb knockout, or Nppb-saporin treated C57BL/6 mice were all treated with IL-31, and the numbers of bouts of scratches were counted. The results are shown in FIG. 7. As shown in FIG. 7, either loss of Nppb or elimination of Npra-neurons leads to marked reduction in responses to the itch agent IL-31. In addition, ISH studies revealed that the receptor for IL-31 is found in the neurons that express Nppb, supporting the concept that Nppb signaling is required for a clinically relevant type of itch.

Example 8

This example demonstrates that administering Nppb to mice induces itch.

In addition to being a key component of the itch neural pathway, Nppb is also produced by the heart and secreted into blood. Nppb controls blood volume and sodium, mainly by regulating sodium secretion by the kidney. In addition, Nppb is a standard biomarker used for diagnosis of heart failure, where elevated Nppb can be measured for up to 48 hours (h) following infarction. Nppb may also be involved in regulating blood volume in response to stress. Very high blood Nppb concentrations are also found in renal failure patients. Accordingly, it was investigated whether there is a causal link between the high circulatory Nppb and itch.

To mimic the high concentration of Nppb found in renal itch patients, mice were i.v. administered Nppb (via tail vein injection). Treated mice exhibited robust whole body scratching behavior. Approximately ten minutes after administration of Nppb, mice began to persistently scratch their flank, face, hind quarters and abdomens. This behavior slowly diminished and almost completely ceased approximately 1 hour after injection. The induction of scratching was dose dependent, with a 1.2 µg/kg dose producing saturating behavioral responses. In all subsequent experiments, a dose of 1.2 µg/kg Nppb (abbreviated as "ivNppb") was used, and bouts of scratching were counted over a period of 1 hour.

It was previously demonstrated that pruriceptive specific spinal cord interneurons express the Nppb-receptor, Npra, and are upstream of itch specific neurons expressing the specific gastrin releasing peptide receptor (GRPR). Npra neurons themselves express GRP and are thought to release GRP which, in turn, activates GRPR-cells. Therefore, a GRP-antagonist was used to show that ivNppb-induced behavior (intrathecal administrated 5 minutes prior to iv Nppb) in fact represented the behavioral correlate of itch-sensation. Notably, it was also found that injection of C-type natriuretic peptide (encoded by the gene Nppc), the selective agonist for the related natriurectic peptide receptor Nprb, produced no observable reaction, showing that this behavior is very specific and indicating that this phenomenon is probably dependent on the Npra. Supporting this hypothesis, ablation of Npra-expressing neurons in the spinal cord with saporin conjugated Nppb toxin eliminated Npra-expressing neurons and abolished ivNppb itch-behavior. Finally, as expected for a centrally acting mechanism, the genetic ablation of all peripheral itch sensory neurons, or elimination of Nppb in sensory neurons, did not affect ivNppb-induced scratch.

Example 9

This example demonstrates that high blood Nppb may causes chronic itch via a neurogenic pathway.

To gain additional evidence that systemic Nppb activates a central itch pathway, the pattern of cellular activation of neurons in the dorsal root ganglion (DRG) and superficial dorsal horn (sDH) was compared by analyzing induction of immediate early gene expression. The skin was stimulated by pruritogen and injections of noxious compounds and the robust induction of immediate early genes, Egr1 and cFos (in the DRG and sDH respectively) was evaluated. Intradermal injection of chloroquine was utilized to excite MrgprA3 peripheral DRG neurons. As expected, ISH analysis showed that administration of chloroquine triggered itch-behavior in mice and induced Egr1 expression in the cell-bodies of a population of DRG neurons. The number of positive Egr-1-positive cells correlated well with the previously reported numbers of MrgprA3-expressing receptor neurons in DRG. Also as expected, injection of the noxious agent, formalin, induced Egr-1 expression in a far larger number and morphologically heterogeneous class of sensory neurons, indicating that different populations of neurons were activated by these different sensory modalities. Likewise, chloroquine and formalin induced cFos expression in different profiles of ipsilateral sDH neurons. Therefore, the initial and later cellular stages of the pruriceptive neural pathway could be reliably monitored biochemically and anatomically and itch signaling could be distinguished from that elicited by the noxious agent formalin.

It was reasoned that if ivNppb was directly activating centrally, then induction of immediate early gene expression would be seen in sDH-neurons and not DRG neurons. Indeed, ISH analysis showed that ivNppb caused cFos induction in the sDH, but importantly did not induce expression of Egr1 in the DRG. As expected from the generalized scratching responses evoked by ivNppb, in both hemispheres of the spinal cord and along the entire length of the spinal cord, cFos-activated neurons could be detected. Furthermore, also consistent with the itch-behavioral result, the profile of cFos-activated neurons in the sDH was similar to that generated by epidermal injection of chloroquine.

Here, molecular, genetic and behavioral assays were used to examine the link between systemic Nppb and itch sensation. Multiple lines of evidence are presented showing that elevated blood Nppb can induce itch through central pathways. Without being bound to a particular theory or mechanism, it is believed that at certain concentrations, systemic Nppb may gain access to the spinal cord and "inadvertently" stimulate itch sensory pathways. Nppb is a small molecule and may gain access to the spinal cord like a number of other small peptides such as opioids that have been reported to gain access to the CNS from the periphery. Under normal circumstances, the body controls blood volume and sodium by making fine adjustments to the level of Nppb. Without being bound to a particular theory or mechanism, it is believed that during kidney failure, the body reacts to elevated blood sodium and blood volume by secreting additional Nppb in an attempt to rectify imbalances in blood sodium and volume. In this condition, a classical positive feedback may develop caused by Nppb-resistance of the kidney. Therefore, without being bound to a particular theory or mechanism, it is believed that high blood Nppb found in uremic itch patient is causal for chronic itch and explains why treatments targeting dermatological origin of itch are largely ineffective. Furthermore, the results suggest that a Nppb-receptor antagonist might be a therapeutic option for treatment of uremic itch.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or reducing pruritis in a mammal in need thereof, the method comprising administering (a) HS-142-1 or (b) [Asu7,23']b-ANA-(7-28)] in an amount effective to treat or reduce pruritis in the mammal.

2. The method of claim 1, wherein the pruritis is associated with a fungal skin infection.

3. The method of claim 1, wherein the pruritis is induced by a pruritogen selected from the group consisting of histamine, chloroquine, endothelin (ET-1), 2-methyl serotonin (5HT), SLIGRL-NH2 (PAR2), and compound 48/80 (48/80).

4. The method of claim 1, wherein the pruritis is associated with renal failure.

5. The method of claim 1, wherein the pruritis is associated with kidney dialysis.

6. The method of claim 1, wherein the pruritis is mediated by interleukin (IL)-31.

7. The method of claim 1, wherein the mammal is a human.

8. The method of claim 1, wherein the pruritis is associated with a Trichomonas skin infection.

9. The method of claim 1, wherein the pruritis is associated with eczema.

10. The method of claim 1, wherein the pruritis is associated with psoriasis.

11. The method of claim 1, wherein the pruritis is associated with acquired immune deficiency syndrome (AIDS).

12. The method of claim 1, wherein the pruritis is associated with polycythemia vera.

13. The method of claim 1, wherein the pruritis is associated with diabetes.

14. The method of claim 1, wherein the pruritis is associated with hyperthyroidism.

15. The method of claim 1, wherein the pruritis is associated with liver damage or liver disease.

16. The method of claim 1, wherein the pruritis is associated with cancer.

17. The method of claim 1, wherein the pruritis is associated with chemotherapy.

18. A method of treating or reducing pruritis in a mammal in need thereof, the method comprising administering [Asu7,23']b-ANA-(7-28)] to the mammal in an amount effective to treat or reduce pruritis in the mammal.

19. The method of claim 18, wherein the pruritis is induced by a pruritogen selected from the group consisting of histamine, chloroquine, endothelin (ET-1), 2-methyl serotonin (5HT), SLIGRL-NH2 (PAR2), and compound 48/80 (48/80).

20. The method of claim 18, wherein the pruritis is associated with a fungal skin infection.

21. The method of claim 18, wherein the pruritis is associated with a Trichomonas skin infection.

22. The method of claim 18, wherein the pruritis is associated with eczema.

23. The method of claim 18, wherein the pruritis is associated with psoriasis.

24. The method of claim 18, wherein the pruritis is associated with renal failure.

25. The method of claim 18, wherein the pruritis is associated with acquired immune deficiency syndrome (AIDS).

26. The method of claim 18, wherein the pruritis is associated with polycythemia vera.

27. The method of claim 18, wherein the pruritis is associated with diabetes.

28. The method of claim 18, wherein the pruritis is associated with hyperthyroidism.

29. The method of claim 4, wherein the pruritis is associated with liver damage or liver disease.

30. The method of claim 18, wherein the pruritis is associated with cancer.

31. The method of claim 18, wherein the pruritis is associated with chemotherapy.

32. The method of claim 18, wherein the pruritis is associated with kidney dialysis.

33. The method of claim 18, wherein the pruritis is mediated by interleukin (IL)-31.

34. The method of claim 18, wherein the mammal is a human.

* * * * *

SEQUENCE LISTING

```
<160> NUMBER OF SEQ ID NOS: 10

<210> SEQ ID NO 1
<211> LENGTH: 708
<212> TYPE: DNA
<213> ORGANISM: Homo sapiens

<400> SEQUENCE: 1
ccccgcaggc tgagggcagg tgggaagcaa acccggacgc atcgcagcag cagcagcagc      60
agcagaagca gcagcagcag cctccgcagt ccctccagag acatggatcc ccagacagca     120
ccttcccggg cgctcctgct cctgctcttc ttgcatctgg ctttcctggg aggtcgttcc     180
cacccgctgg gcagccccgg ttcagcctcg gacttggaaa cgtccgggtt acaggagcag     240
cgcaaccatt tgcagggcaa actgtcggag ctgcaggtgg agcagacatc cctggagccc     300
ctccaggaga gcccccgtcc cacaggtgtc tggaagtccc gggaggtagc caccgagggc     360
atccgtgggc accgcaaaat ggtcctctac accctgcggg caccacgaag ccccaagatg     420
gtgcaagggt ctggctgctt tgggaggaag atggaccgga tcagctcctc cagtggcctg     480
ggctgcaaag tgctgaggcg gcattaagag gaagtcctgg ctgcagacac ctgcttctga     540
ttccacaagg ggcttttttcc tcaaccctgt ggccgccttt gaagtgactc attttttttaa     600 tgtatttatg tatttatttg attgttttat ataagatggt ttcttacctt tgagcacaaa     660
atttccacgg tgaaataaag tcaacattat aagctttaaa aaaaaaaa                  708

<210> SEQ ID NO 2
<211> LENGTH: 134
<212> TYPE: PRT
<213> ORGANISM: Homo sapiens

<400> SEQUENCE: 2

Met Asp Pro Gln Thr Ala Pro Ser Arg Ala Leu Leu Leu Leu Leu Phe
  1               5                  10                  15

Leu His Leu Ala Phe Leu Gly Gly Arg Ser His Pro Leu Gly Ser Pro
             20                  25                  30

Gly Ser Ala Ser Asp Leu Glu Thr Ser Gly Leu Gln Glu Gln Arg Asn
         35                  40                  45
```

```
His Leu Gln Gly Lys Leu Ser Glu Leu Gln Val Gln Thr Ser Leu
     50                  55                  60

Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                 85                  90                  95

Thr Leu Arg Ala Pro Arg Ser Pro Lys Met Val Gln Gly Ser Gly Cys
             100                 105                 110

Phe Gly Arg Lys Met Asp Arg Ile Ser Ser Ser Gly Leu Gly Cys
             115                 120                 125

Lys Val Leu Arg Arg His
         130

<210> SEQ ID NO 3
<211> LENGTH: 4201
<212> TYPE: DNA
<213> ORGANISM: Homo sapiens

<400> SEQUENCE: 3
```

| | | | | | |
|---|---|---|---|---|---|
| acactccctg | gggcaggcgc | tcacgcacgc | tacaaacaca | cactcctctt | tcctccctcg | 60 |
| cgcgccctct | ctcatccttc | ttcacgaagc | gctcactcgc | acccttctc | tctctctctc | 120 |
| tctctctcta | acacgcacgc | acactcccag | ttgttcacac | tcgggtcctc | tccagcccga | 180 |
| cgttctcctg | gcacccacct | gctccgcggc | gccctgcgcg | cccccctcgg | tcgcgcccct | 240 |
| tgcgctctcg | gcccagaccg | tcgcagctac | aggggggcctc | gagccccggg | gtgagcgtcc | 300 |
| ccgtcccgct | cctgctcctt | cccatagga | gcgcctgat | gcctgggacc | ggccgctgag | 360 |
| cccaaggga | ccgaggaggc | catggtagga | gcgctcgcct | gctgcggtgc | ccgctgaggc | 420 |
| catgccgggg | ccccggcgcc | ccgctggctc | ccgcctgcgc | ctgctcctgc | tcctgctgct | 480 |
| gccgccgctg | ctgctgctgc | tccggggcag | ccacgcgggc | aacctgacgg | tagccgtggt | 540 |
| actgccgctg | gccaataacct | cgtaccctg | gtcgtgggcg | cgcgtgggac | ccgccgtgga | 600 |
| gctggccctg | gccaggtga | aggcgcgccc | cgacttgctg | ccgggctgga | cggtccgcac | 660 |
| ggtgctgggc | agcagcgaaa | acgcgctggg | cgtctgctcc | gacaccgcag | cgccctggc | 720 |
| cgcggtggac | ctcaagtggg | agcacaaccc | cgctgtgttc | ctgggccccg | gctgcgtgta | 780 |
| cgccgccgcc | ccagtgggc | gcttcaccgc | gcactggcgg | gtcccgctgc | tgaccgccgg | 840 |
| cgcccccggcg | ctgggcttcg | gtgtcaagga | cgagtatgcg | ctgaccaccc | gcgcggggcc | 900 |
| cagctacgcc | aagctggggg | acttcgtggc | ggcgctgcac | cgacggctgg | gctgggagcg | 960 |
| ccaagcgctc | atgctctacg | cctaccggcc | gggtgacgaa | gagcactgct | tcttcctcgt | 1020 |
| ggaggggctg | ttcatgcggg | tccgcgaccg | cctcaatatt | acgtggacc | acctggagtt | 1080 |
| cgccgaggac | gacctcagcc | actacaccag | gctgctgcgg | accatgccgc | gcaaaggccg | 1140 |
| agttatctac | atctgcagct | cccctgatgc | cttcagaacc | ctcatgctcc | tggccctgga | 1200 |
| agctggcttg | tgtggggagg | actacgtttt | cttccacctg | gatatctttg | gcaaagcct | 1260 |
| gcaaggtgga | cagggccctg | ctccccgcag | gccctgggag | agaggggatg | gcaggatgt | 1320 |
| cagtgcccgc | caggccttc | aggctgccaa | aatcattaca | tataaagacc | cagataatcc | 1380 |
| cgagtacttg | gaattcctga | agcagttaaa | acacctggcc | tatgagcagt | caacttcac | 1440 |
| catggaggat | ggcctggtga | acaccatccc | agcatcctc | cacgacgggc | tcctgctcta | 1500 |
| tatccaggca | gtgacggaga | ctctggcaca | tggggaact | gttactgatg | gggagaacat | 1560 |

```
cactcagcgg atgtggaacc gaagctttca aggtgtgaca ggatacctga aaattgatag    1620
cagtggcgat cgggaaacag acttctccct ctgggatatg gatcccgaga atggtgcctt    1680
cagggttgta ctgaactaca atgggacttc ccaagagctg gtggctgtgt cggggcgcaa    1740
actgaactgg cccctgggt accctcctcc tgacatcccc aaatgtggct ttgacaacga    1800
agacccagca tgcaaccaag atcaccttc caccctggag gtgctggctt tggtgggcag    1860
cctctccttg ctcggcattc tgattgtctc cttcttcata tacaggaaga tgcagctgga    1920
gaaggaactg gcctcggagc tgtggcgggt cgctgggag gacgttgagc ccagtagcct    1980
tgagaggcac ctgcggagtg caggcagccg gctgaccctg agcggagag ctccaatta    2040
cggctccctg ctaaccacag agggccagtt ccaagtcttt gccaagacag catattataa    2100
gggcaacctc gtggctgtga aacgtgtgaa ccgtaaacgc attgagctga cacgaaaagt    2160
cctgtttgaa ctgaagcata tgcgggatgt gcagaatgaa caacctgacca ggtttgtggg    2220
agcctgcacc gaccccccca atatctgcat cctcacagag tactgtcccc gtgggagcct    2280
gcaggacatt ctgagaatg agagcatcac cctggactgg atgttccggt actcactcac    2340
caatgacatc gtcaagggca tgctgttct acacaatggg gctatctgtt cccatgggaa    2400
cctcaagtca tccaactgcg tggtagatgg gcgctttgtg ctcaagatca ccgactatgg    2460
gctggagagc ttcagggacc tggacccaga gcaaggacac accgtttatg ccaaaaagct    2520
gtggacggcc cctgagctcc tgcgaatggc ttcaccccct gtgcggggct cccaggctgg    2580
tgacgtatac agctttggga tcatccttca ggagattgcc ctgaggagtg ggtcttcca    2640
cgtggaaggt ttgacctga gccccaaaga gatcatcgag cgggtgactc ggggtgagca    2700
gccccccttc cggccctccc tggccctgca gagtcacctg gaggagttgg ggctgctcat    2760
gcagcggtgc tgggctgagg acccacagga gaggccacca ttccagcaga tccgcctgac    2820
gttgcgcaaa tttaacaggg agaacagcag caacatcctg gacaacctgc tgtcccgcat    2880
ggagcagtac gcgaacaatc tggaggaact ggtggaggag cggacccagg catacctgga    2940
ggagaagcgc aaggctgagg ccctgctcta ccagatcctg cctcactcag tggctgagca    3000
gctgaagcgt ggggagacgg tgcaggccga agcctttgac agtgttacca tctacttcag    3060
tgacattgtg ggtttcacag cgctgtcggc ggagagcaca cccatgcagg tggtgaccct    3120
gctcaatgac ctgtacactt gctttgatgc tgtcatagac aactttgatg tgtacaaggt    3180
ggagacaatt ggcgatgcct acatggtggt gtcagggctc cctgtgcgga acgggcggct    3240
acacgcctgc gaggtagccc gcatggccct ggcactgctg atgctgtgc gctccttccg    3300
aatccgccac cggccccagg agcagctgcg cttgcgcatt ggcatccaca caggacctgt    3360
gtgtgctgga gtggtgggac tgaagatgcc ccgttactgt ctctttgggg atacagtcaa    3420
cacagcctca agaatggagt ctaatgggga agccctgaag atccacttgt cttctgagac    3480
caaggctgtc ctggaggagt ttggtggttt cgagctggag cttcgagggg atgtagaaat    3540
gaagggcaaa ggcaaggttc ggacctactg gctccttggg gagagggga gtagcacccg    3600
aggctgacct gcctcctctc ctatccctcc acacctccct accctgtgcc agaagcaaca    3660
gaggtgccag gcctcagcct cacccacagc agccccatcg ccaaaggatg gaagtaattt    3720
gaatagctca ggtgtgctga ccccagtgaa gacaccagat aggacctctg agagggact    3780
ggcatggggg gatctcagag cttacaggct gagccaagcc cacggccatg cacagggaca    3840
ctcacacagg cacacgcacc tgctctccac ctggactcag gccgggctgg gctgtggatt    3900
cctgatcccc tcccctcccc atgctctcct ccctcagcct tgctaccctg tgacttactg    3960
```

-continued

```
ggaggagaaa gagtcacctg aagggaaca tgaaaagaga ctaggtgaag agagggcagg    4020
ggagcccaca tctggggctg gcccacaata cctgctcccc cgaccccctc cacccagcag    4080
tagacacagt gcacagggga aagaggggt ggcgcagaag ggttgggggc ctgtatgcct    4140
tgcttctacc atgagcagag acaattaaaa tctttattcc agtgaaaaaa aaaaaaaaaa    4200
a                                                                    4201
```

<210> SEQ ID NO 4
<211> LENGTH: 1061
<212> TYPE: PRT
<213> ORGANISM: Homo sapiens

<400> SEQUENCE: 4

```
Met Pro Gly Pro Arg Arg Pro Ala Gly Ser Arg Leu Arg Leu Leu Leu
1               5                   10                  15

Leu Leu Leu Leu Pro Pro Leu Leu Leu Leu Leu Arg Gly Ser His Ala
                20                  25                  30

Gly Asn Leu Thr Val Ala Val Val Leu Pro Leu Ala Asn Thr Ser Tyr
            35                  40                  45

Pro Trp Ser Trp Ala Arg Val Gly Pro Ala Val Glu Leu Ala Leu Ala
        50                  55                  60

Gln Val Lys Ala Arg Pro Asp Leu Leu Pro Gly Trp Thr Val Arg Thr
65                  70                  75                  80

Val Leu Gly Ser Ser Glu Asn Ala Leu Gly Val Cys Ser Asp Thr Ala
                85                  90                  95

Ala Pro Leu Ala Ala Val Asp Leu Lys Trp Glu His Asn Pro Ala Val
            100                 105                 110

Phe Leu Gly Pro Gly Cys Val Tyr Ala Ala Pro Val Gly Arg Phe
        115                 120                 125

Thr Ala His Trp Arg Val Pro Leu Leu Thr Ala Gly Ala Pro Ala Leu
130                 135                 140

Gly Phe Gly Val Lys Asp Glu Tyr Ala Leu Thr Thr Arg Ala Gly Pro
145                 150                 155                 160

Ser Tyr Ala Lys Leu Gly Asp Phe Val Ala Ala Leu His Arg Arg Leu
                165                 170                 175

Gly Trp Glu Arg Gln Ala Leu Met Leu Tyr Ala Tyr Arg Pro Gly Asp
            180                 185                 190

Glu Glu His Cys Phe Phe Leu Val Glu Gly Leu Phe Met Arg Val Arg
        195                 200                 205

Asp Arg Leu Asn Ile Thr Val Asp His Leu Glu Phe Ala Glu Asp Asp
    210                 215                 220

Leu Ser His Tyr Thr Arg Leu Leu Arg Thr Met Pro Arg Lys Gly Arg
225                 230                 235                 240

Val Ile Tyr Ile Cys Ser Ser Pro Asp Ala Phe Arg Thr Leu Met Leu
                245                 250                 255

Leu Ala Leu Glu Ala Gly Leu Cys Gly Glu Asp Tyr Val Phe Phe His
            260                 265                 270

Leu Asp Ile Phe Gly Gln Ser Leu Gln Gly Gly Gln Gly Pro Ala Pro
        275                 280                 285

Arg Arg Pro Trp Glu Arg Gly Asp Gly Gln Asp Val Ser Ala Arg Gln
    290                 295                 300

Ala Phe Gln Ala Ala Lys Ile Ile Thr Tyr Lys Asp Pro Asp Asn Pro
305                 310                 315                 320
```

-continued

```
Glu Tyr Leu Glu Phe Leu Lys Gln Leu Lys His Leu Ala Tyr Glu Gln
                325                 330                 335

Phe Asn Phe Thr Met Glu Asp Gly Leu Val Asn Thr Ile Pro Ala Ser
            340                 345                 350

Phe His Asp Gly Leu Leu Leu Tyr Ile Gln Ala Val Thr Glu Thr Leu
        355                 360                 365

Ala His Gly Gly Thr Val Thr Asp Gly Glu Asn Ile Thr Gln Arg Met
    370                 375                 380

Trp Asn Arg Ser Phe Gln Gly Val Thr Gly Tyr Leu Lys Ile Asp Ser
385                 390                 395                 400

Ser Gly Asp Arg Glu Thr Asp Phe Ser Leu Trp Asp Met Asp Pro Glu
                405                 410                 415

Asn Gly Ala Phe Arg Val Val Leu Asn Tyr Asn Gly Thr Ser Gln Glu
            420                 425                 430

Leu Val Ala Val Ser Gly Arg Lys Leu Asn Trp Pro Leu Gly Tyr Pro
        435                 440                 445

Pro Pro Asp Ile Pro Lys Cys Gly Phe Asp Asn Glu Asp Pro Ala Cys
    450                 455                 460

Asn Gln Asp His Leu Ser Thr Leu Glu Val Leu Ala Leu Val Gly Ser
465                 470                 475                 480

Leu Ser Leu Leu Gly Ile Leu Ile Val Ser Phe Phe Ile Tyr Arg Lys
                485                 490                 495

Met Gln Leu Glu Lys Glu Leu Ala Ser Glu Leu Trp Arg Val Arg Trp
            500                 505                 510

Glu Asp Val Glu Pro Ser Ser Leu Glu Arg His Leu Arg Ser Ala Gly
        515                 520                 525

Ser Arg Leu Thr Leu Ser Gly Arg Gly Ser Asn Tyr Gly Ser Leu Leu
    530                 535                 540

Thr Thr Glu Gly Gln Phe Gln Val Phe Ala Lys Thr Ala Tyr Tyr Lys
545                 550                 555                 560

Gly Asn Leu Val Ala Val Lys Arg Val Asn Arg Lys Arg Ile Glu Leu
                565                 570                 575

Thr Arg Lys Val Leu Phe Glu Leu Lys His Met Arg Asp Val Gln Asn
            580                 585                 590

Glu His Leu Thr Arg Phe Val Gly Ala Cys Thr Asp Pro Pro Asn Ile
        595                 600                 605

Cys Ile Leu Thr Glu Tyr Cys Pro Arg Gly Ser Leu Gln Asp Ile Leu
    610                 615                 620

Glu Asn Glu Ser Ile Thr Leu Asp Trp Met Phe Arg Tyr Ser Leu Thr
625                 630                 635                 640

Asn Asp Ile Val Lys Gly Met Leu Phe Leu His Asn Gly Ala Ile Cys
                645                 650                 655

Ser His Gly Asn Leu Lys Ser Ser Asn Cys Val Val Asp Gly Arg Phe
            660                 665                 670

Val Leu Lys Ile Thr Asp Tyr Gly Leu Glu Ser Phe Arg Asp Leu Asp
        675                 680                 685

Pro Glu Gln Gly His Thr Val Tyr Ala Lys Lys Leu Trp Thr Ala Pro
    690                 695                 700

Glu Leu Leu Arg Met Ala Ser Pro Pro Val Arg Gly Ser Gln Ala Gly
705                 710                 715                 720

Asp Val Tyr Ser Phe Gly Ile Ile Leu Gln Glu Ile Ala Leu Arg Ser
                725                 730                 735

Gly Val Phe His Val Glu Gly Leu Asp Leu Ser Pro Lys Glu Ile Ile
```

740                 745                 750
Glu Arg Val Thr Arg Gly Glu Gln Pro Pro Phe Arg Pro Ser Leu Ala
                755                 760                 765
Leu Gln Ser His Leu Glu Glu Leu Gly Leu Leu Met Gln Arg Cys Trp
            770                 775                 780
Ala Glu Asp Pro Gln Glu Arg Pro Pro Phe Gln Gln Ile Arg Leu Thr
785                 790                 795                 800
Leu Arg Lys Phe Asn Arg Glu Asn Ser Ser Asn Ile Leu Asp Asn Leu
                805                 810                 815
Leu Ser Arg Met Glu Gln Tyr Ala Asn Asn Leu Glu Glu Leu Val Glu
            820                 825                 830
Glu Arg Thr Gln Ala Tyr Leu Glu Glu Lys Arg Lys Ala Glu Ala Leu
            835                 840                 845
Leu Tyr Gln Ile Leu Pro His Ser Val Ala Glu Gln Leu Lys Arg Gly
            850                 855                 860
Glu Thr Val Gln Ala Glu Ala Phe Asp Ser Val Thr Ile Tyr Phe Ser
865                 870                 875                 880
Asp Ile Val Gly Phe Thr Ala Leu Ser Ala Glu Ser Thr Pro Met Gln
                885                 890                 895
Val Val Thr Leu Leu Asn Asp Leu Tyr Thr Cys Phe Asp Ala Val Ile
            900                 905                 910
Asp Asn Phe Asp Val Tyr Lys Val Glu Thr Ile Gly Asp Ala Tyr Met
            915                 920                 925
Val Val Ser Gly Leu Pro Val Arg Asn Gly Arg Leu His Ala Cys Glu
            930                 935                 940
Val Ala Arg Met Ala Leu Ala Leu Leu Asp Ala Val Arg Ser Phe Arg
945                 950                 955                 960
Ile Arg His Arg Pro Gln Glu Gln Leu Arg Leu Arg Ile Gly Ile His
                965                 970                 975
Thr Gly Pro Val Cys Ala Gly Val Val Gly Leu Lys Met Pro Arg Tyr
            980                 985                 990
Cys Leu Phe Gly Asp Thr Val Asn Thr Ala Ser Arg Met Glu Ser Asn
            995                 1000                1005
Gly Glu Ala Leu Lys Ile His Leu Ser Ser Glu Thr Lys Ala Val
        1010            1015            1020
Leu Glu Glu Phe Gly Gly Phe Glu Leu Glu Leu Arg Gly Asp Val
        1025            1030            1035
Glu Met Lys Gly Lys Gly Lys Val Arg Thr Tyr Trp Leu Leu Gly
        1040            1045            1050
Glu Arg Gly Ser Ser Thr Arg Gly
        1055            1060

<210> SEQ ID NO 5
<211> LENGTH: 4178
<212> TYPE: DNA
<213> ORGANISM: Homo sapiens

<400> SEQUENCE: 5
gcttggctcg ggtcctccac ggttccctcc ggatagccgg agacttgggc cggccggacg      60
ccccttctgg cacactccct ggggcaggcg ctcacgcacg ctacaaacac acactcctct     120
ttcctccctc gcgcgccctc tctcatcctt cttcacgaag cgctcactcg cacccttttct    180 ctctctctct ctctctctct aacacgcacg cacactccca gttgttcaca ctcgggtcct    240
ctccagcccg acgttctcct ggcacccacc tgctccgcgg cgccctgcgc gccccccctcg   300

```
gtcgcgcccc ttgcgctctc ggcccagacc gtcgcagcta caggggggcct cgagccccgg      360 ggtgagcgtc cccgtcccgc tcctgctcct tcccataggg acgcgcctga tgcctgggac      420
cggccgctga gcccaagggg accgaggagg ccatggtagg agcgctcgcc tgctgcggtg      480
cccgctgagg ccatgccggg gccccggcgc cccgctggct cccgcctgcg cctgctcctg      540
ctcctgctgc tgccgccgct gctgctgctg ctccggggca gccacgcggg caacctgacg      600
gtagccgtgt actgccgct ggccaatacc tcgtacccct ggtcgtgggc gcgcgtggga       660
cccgccgtgg agctggccct ggcccaggtg aaggcgcgcc ccgacttgct gccgggctgg      720
acggtccgca cggtgctggg cagcagcgaa acgcgctggg cgtctgctc cgacaccgca       780 gcgcccctgg ccgcggtgga cctcaagtgg gagcacaacc ccgctgtgtt cctgggcccc      840
ggctgcgtgt acgccgccgc cccagtgggg cgcttcaccg cgcactggcg ggtcccgctg      900
ctgaccgccg gcgccccggc gctgggcttc ggtgtcaagg acgagtatgc gctgaccacc      960
cgcgcggggc ccagctacgc caagctgggg gacttcgtgg cggcgctgca ccgacggctg      1020
ggctgggagc gccaagcgct catgctctac gcctaccggc cgggtgacga agagcactgc      1080
ttcttcctcg tggaggggct gttcatgcgg gtccgcgacc gcctcaatat tacggtggac      1140
cacctggagt tcgccgagga cgacctcagc cactacacca ggctgctgcg gaccatgccg      1200
cgcaaaggcc gagttatcta catctgcagc tcccctgatg ccttcagaac cctcatgctc      1260
ctggccctgg aagctggctt gtgtgtgggag gactacgttt tcttccacct ggatatcttt      1320
gggcaaagcc tgcaaggtgg acagggccct gctccccgca ggccctggga gagagggggat     1380 gggcaggatg tcagtgcccg ccaggccttt caggctgcca aaatcattac atataaagac      1440
ccagataatc ccgagtactt ggaattcctg aagcagttaa acacctggc ctatgagcag       1500 ttcaacttca ccatggagga tggcctggtg aacaccatcc cagcatcctt ccacgacggg      1560
ctcctgctct atatccaggc agtgacggag actctggcac atgggggaac tgttactgat      1620
ggggagaaca tcactcagcg gatgtggaac cgaagctttc aaggtgtgac aggatacctg      1680
aaaattgata gcagtggcga tcgggaaaca gacttctccc tctgggatat ggatcccgag      1740
aatggtgcct tcagggttgt actgaactac aatgggactt cccaagagct ggtggctgtg      1800
tcggggcgca aactgaactg gccccctgggg taccctcctc ctgacatccc caaatgtggc      1860
tttgacaacg aagacccagc atgcaaccaa gatcacctttt ccaccctgga ggtgctggct     1920
ttggtgggca gcctctcctt gctcggcatt ctgattgtct ccttcttcat atacaggaag      1980
atgcagctga gaaggaact ggcctcgag ctgtggcggg tgcgctggga ggacgttgag        2040
cccagtagcc ttgagaggca cctgcggagt gcaggcagcc ggctgaccct gagcgggaga      2100
ggctccaatt acggctccct gctaaccaca gagggccagt ccaagtctt tgccaagaca      2160 gcatattata agatgcggga tgtgcagaat gaacacctga ccaggtttgt gggagcctgc      2220
accgaccccc ccaatatctg catcctcaca gagtactgtc cccgtgggag cctgcaggac     2280
attctggaga atgagagcat caccctggac tggatgttcc ggtactcact caccaatgac     2340
atcgtcaagg gcatgctgtt tctacacaat ggggctatct gttcccatgg gaacctcaag      2400
tcatccaact gcgtggtaga tgggcgcttt gtgctcaaga tcaccgacta tgggctggag      2460
agcttcaggg acctggaccc agagcaagga cacaccgttt atgccaaaaa gctgtggacg      2520
gcccctgagc tcctgcgaat ggcttcaccc cctgtgcggg gctcccaggc tggtgacgta      2580
tacagctttg ggatcatcct tcaggagatt gccctgagga gtgggtctt ccacgtggaa       2640
```

-continued

| | |
|---|---|
| ggtttggacc tgagcccaa agagatcatc gagcgggtga ctcggggtga gcagcccccc | 2700 |
| ttccggccct ccctggccct gcagagtcac ctggaggagt tggggctgct catgcagcgg | 2760 |
| tgctgggctg aggacccaca ggagaggcca ccattccagc agatccgcct gacgttgcgc | 2820 |
| aaatttaaca gggagaacag cagcaacatc ctggacaacc tgctgtcccg catggagcag | 2880 |
| tacgcgaaca atctggagga actggtggag gagcggaccc aggcatacct ggaggagaag | 2940 |
| cgcaaggctg aggccctgct ctaccagatc ctgcctcact cagtggctga gcagctgaag | 3000 |
| cgtggggaga cggtgcaggc cgaagccttt gacagtgtta ccatctactt cagtgacatt | 3060 |
| gtgggtttca cagcgctgtc ggcggagagc acacccatgc aggtggtgac cctgctcaat | 3120 |
| gacctgtaca cttgctttga tgctgtcata gacaactttg atgtgtacaa ggtggagaca | 3180 |
| attggcgatg cctacatggt ggtgtcaggg ctccctgtgc ggaacgggcg gctacacgcc | 3240 |
| tgcgaggtag cccgcatggc cctggcactg ctggatgctg tgcgctcctt ccgaatccgc | 3300 |
| caccggcccc aggagcagct gcgcttgcgc attggcatcc acacaggacc tgtgtgtgct | 3360 |
| ggagtggtgg gactgaagat gccccgttac tgtctctttg gggatacagt caacacagcc | 3420 |
| tcaagaatgg agtctaatgg ggaagccctg aagatccact tgtcttctga gaccaaggct | 3480 |
| gtcctggagg agtttggtgg tttcgagctg agcttcgag gggatgtaga aatgaagggc | 3540 |
| aaaggcaagg ttcggaccta ctggctcctt ggggagaggg ggagtagcac ccgaggctga | 3600 |
| cctgcctcct ctcctatccc tccacacctc cctaccctgt gccagaagca acagaggtgc | 3660 |
| caggcctcag cctcacccac agcagcccca tcgccaaagg atggaagtaa tttgaatagc | 3720 |
| tcaggtgtgc tgaccccagt gaagacacca gataggacct ctgagagggg actggcatgg | 3780 |
| ggggatctca gagcttacag gctgagccaa gcccacggcc atgcacaggg acactcacac | 3840 |
| aggcacacgc acctgctctc cacctggact caggccgggc tgggctgtgg attcctgatc | 3900 |
| ccctcccctc ccatgctctc cctccctcag ccttgctacc ctgtgactta ctgggaggag | 3960 |
| aaagagtcac ctgaagggga acatgaaaag agactaggtg aagagagggc aggggagccc | 4020 |
| acatctgggg ctggcccaca atacctgctc ccccgacccc ctccacccag cagtagacac | 4080 |
| agtgcacagg ggagaagagg ggtggcgcag aagggttggg ggcctgtatg ccttgcttct | 4140 |
| accatgagca gagacaatta aaatctttat tccagtga | 4178 |

<210> SEQ ID NO 6
<211> LENGTH: 1035
<212> TYPE: PRT
<213> ORGANISM: Homo sapiens

<400> SEQUENCE: 6

```
Met Pro Gly Pro Arg Arg Pro Ala Gly Ser Arg Leu Arg Leu Leu Leu
1               5                   10                  15

Leu Leu Leu Leu Pro Pro Leu Leu Leu Leu Leu Arg Gly Ser His Ala
                20                  25                  30

Gly Asn Leu Thr Val Ala Val Val Leu Pro Leu Ala Asn Thr Ser Tyr
            35                  40                  45

Pro Trp Ser Trp Ala Arg Val Gly Pro Ala Val Glu Leu Ala Leu Ala
        50                  55                  60

Gln Val Lys Ala Arg Pro Asp Leu Leu Pro Gly Trp Thr Val Arg Thr
65                  70                  75                  80

Val Leu Gly Ser Ser Glu Asn Ala Leu Gly Val Cys Ser Asp Thr Ala
                85                  90                  95

Ala Pro Leu Ala Ala Val Asp Leu Lys Trp Glu His Asn Pro Ala Val
```

```
              100                 105                 110
Phe Leu Gly Pro Gly Cys Val Tyr Ala Ala Pro Val Gly Arg Phe
            115                 120                 125
Thr Ala His Trp Arg Val Pro Leu Leu Thr Gly Ala Pro Ala Leu
            130                 135             140
Gly Phe Gly Val Lys Asp Glu Tyr Ala Leu Thr Arg Ala Gly Pro
145                 150                 155                 160
Ser Tyr Ala Lys Leu Gly Asp Phe Val Ala Leu His Arg Arg Leu
                165                 170                 175
Gly Trp Glu Arg Gln Ala Leu Met Leu Tyr Ala Tyr Arg Pro Gly Asp
                180                 185                 190
Glu Glu His Cys Phe Phe Leu Val Glu Gly Leu Phe Met Arg Val Arg
                195                 200                 205
Asp Arg Leu Asn Ile Thr Val Asp His Leu Glu Phe Ala Glu Asp Asp
                210                 215                 220
Leu Ser His Tyr Thr Arg Leu Leu Arg Thr Met Pro Arg Lys Gly Arg
225                 230                 235                 240
Val Ile Tyr Ile Cys Ser Ser Pro Asp Ala Phe Arg Thr Leu Met Leu
                245                 250                 255
Leu Ala Leu Glu Ala Gly Leu Cys Gly Glu Asp Tyr Val Phe Phe His
                260                 265                 270
Leu Asp Ile Phe Gly Gln Ser Leu Gln Gly Gly Gln Gly Pro Ala Pro
                275                 280                 285
Arg Arg Pro Trp Glu Arg Gly Asp Gly Gln Asp Val Ser Ala Arg Gln
                290                 295                 300
Ala Phe Gln Ala Ala Lys Ile Ile Thr Tyr Lys Asp Pro Asp Asn Pro
305                 310                 315                 320
Glu Tyr Leu Glu Phe Leu Lys Gln Leu Lys His Leu Ala Tyr Glu Gln
                325                 330                 335
Phe Asn Phe Thr Met Glu Asp Gly Leu Val Asn Thr Ile Pro Ala Ser
                340                 345                 350
Phe His Asp Gly Leu Leu Leu Tyr Ile Gln Ala Val Thr Glu Thr Leu
                355                 360                 365
Ala His Gly Gly Thr Val Thr Asp Gly Glu Asn Ile Thr Gln Arg Met
                370                 375             380
Trp Asn Arg Ser Phe Gln Gly Val Thr Gly Tyr Leu Lys Ile Asp Ser
385                 390                 395                 400
Ser Gly Asp Arg Glu Thr Asp Phe Ser Leu Trp Asp Met Asp Pro Glu
                405                 410                 415
Asn Gly Ala Phe Arg Val Val Leu Asn Tyr Asn Gly Thr Ser Gln Glu
                420                 425                 430
Leu Val Ala Val Ser Gly Arg Lys Leu Asn Trp Pro Leu Gly Tyr Pro
                435                 440                 445
Pro Pro Asp Ile Pro Lys Cys Gly Phe Asp Asn Glu Asp Pro Ala Cys
                450                 455                 460
Asn Gln Asp His Leu Ser Thr Leu Glu Val Leu Ala Leu Val Gly Ser
465                 470                 475                 480
Leu Ser Leu Leu Gly Ile Leu Ile Val Ser Phe Phe Ile Tyr Arg Lys
                485                 490                 495
Met Gln Leu Glu Lys Glu Leu Ala Ser Glu Leu Trp Arg Val Arg Trp
                500                 505                 510
Glu Asp Val Glu Pro Ser Ser Leu Glu Arg His Leu Arg Ser Ala Gly
                515                 520                 525
```

```
Ser Arg Leu Thr Leu Ser Gly Arg Gly Ser Asn Tyr Gly Ser Leu Leu
    530                 535                 540
Thr Thr Glu Gly Gln Phe Gln Val Phe Ala Lys Thr Ala Tyr Tyr Lys
545                 550                 555                 560
Met Arg Asp Val Gln Asn Glu His Leu Thr Arg Phe Val Gly Ala Cys
                565                 570                 575
Thr Asp Pro Pro Asn Ile Cys Ile Leu Thr Glu Tyr Cys Pro Arg Gly
            580                 585                 590
Ser Leu Gln Asp Ile Leu Glu Asn Glu Ser Ile Thr Leu Asp Trp Met
        595                 600                 605
Phe Arg Tyr Ser Leu Thr Asn Asp Ile Val Lys Gly Met Leu Phe Leu
    610                 615                 620
His Asn Gly Ala Ile Cys Ser His Gly Asn Leu Lys Ser Ser Asn Cys
625                 630                 635                 640
Val Val Asp Gly Arg Phe Val Leu Lys Ile Thr Asp Tyr Gly Leu Glu
                645                 650                 655
Ser Phe Arg Asp Leu Asp Pro Glu Gln Gly His Thr Val Tyr Ala Lys
            660                 665                 670
Lys Leu Trp Thr Ala Pro Glu Leu Leu Arg Met Ala Ser Pro Pro Val
        675                 680                 685
Arg Gly Ser Gln Ala Gly Asp Val Tyr Ser Phe Gly Ile Ile Leu Gln
    690                 695                 700
Glu Ile Ala Leu Arg Ser Gly Val Phe His Val Glu Gly Leu Asp Leu
705                 710                 715                 720
Ser Pro Lys Glu Ile Ile Glu Arg Val Thr Arg Gly Glu Gln Pro Pro
                725                 730                 735
Phe Arg Pro Ser Leu Ala Leu Gln Ser His Leu Glu Glu Leu Gly Leu
            740                 745                 750
Leu Met Gln Arg Cys Trp Ala Glu Asp Pro Gln Glu Arg Pro Pro Phe
        755                 760                 765
Gln Gln Ile Arg Leu Thr Leu Arg Lys Phe Asn Arg Glu Asn Ser Ser
    770                 775                 780
Asn Ile Leu Asp Asn Leu Leu Ser Arg Met Glu Gln Tyr Ala Asn Asn
785                 790                 795                 800
Leu Glu Glu Leu Val Glu Glu Arg Thr Gln Ala Tyr Leu Glu Glu Lys
                805                 810                 815
Arg Lys Ala Glu Ala Leu Leu Tyr Gln Ile Leu Pro His Ser Val Ala
            820                 825                 830
Glu Gln Leu Lys Arg Gly Glu Thr Val Gln Ala Glu Ala Phe Asp Ser
        835                 840                 845
Val Thr Ile Tyr Phe Ser Asp Ile Val Gly Phe Thr Ala Leu Ser Ala
    850                 855                 860
Glu Ser Thr Pro Met Gln Val Val Thr Leu Leu Asn Asp Leu Tyr Thr
865                 870                 875                 880
Cys Phe Asp Ala Val Ile Asp Asn Phe Asp Val Tyr Lys Val Glu Thr
                885                 890                 895
Ile Gly Asp Ala Tyr Met Val Val Ser Gly Leu Pro Val Arg Asn Gly
            900                 905                 910
Arg Leu His Ala Cys Glu Val Ala Arg Met Ala Leu Ala Leu Leu Asp
        915                 920                 925
Ala Val Arg Ser Phe Arg Ile Arg His Arg Pro Gln Glu Gln Leu Arg
    930                 935                 940
```

```
Leu Arg Ile Gly Ile His Thr Gly Pro Val Cys Ala Gly Val Val Gly
945                 950                 955                 960

Leu Lys Met Pro Arg Tyr Cys Leu Phe Gly Asp Thr Val Asn Thr Ala
                965                 970                 975

Ser Arg Met Glu Ser Asn Gly Glu Ala Leu Lys Ile His Leu Ser Ser
            980                 985                 990

Glu Thr Lys Ala Val Leu Glu Glu Phe Gly Gly Phe Glu Leu Glu Leu
        995                 1000                1005

Arg Gly Asp Val Glu Met Lys Gly Lys Gly Lys Val Arg Thr Tyr
    1010                1015                1020

Trp Leu Leu Gly Glu Arg Gly Ser Ser Thr Arg Gly
    1025                1030                1035

<210> SEQ ID NO 7
<211> LENGTH: 797
<212> TYPE: DNA
<213> ORGANISM: Mus musculus

<400> SEQUENCE: 7
ccggcaggaa tgcagctgat aaatcagaga taaccccacc cctactccgt gaaaaggtct      60
ggccggacac tcagccccag tataaaaggc agaggcaccg ttgttgaaga caccagtgca     120
caagctgctt ggggaggcga dacaaggggag aacacggcat cattgcctgg cccatcgctt     180
ctgcggcatg gatctcctga aggtgctgtc ccagatgatt ctgtttctgc ttttccttta     240
tctgtcaccg ctgggaggtc actcctatcc tctgggaagt cctagccagt ctccagagca     300
attcaagatg cagaagctgc tggagctgat aagagaaaag tcggaggaaa tggcccagag     360
acagctcttg aaggaccaag gcctcacaaa agaacaccca aaaagagtcc ttcggtctca     420
aggcagcacc ctccgggtcc agcagagacc tcaaaattcc aaggtgacac atatctcaag     480
ctgctttggg cacaagatag accggatcgg atccgtcagt cgtttgggct gtaacgcact     540
gaagttgttg taggaagacc tcctggctgc aggagactcc agtttctgac tctgcctggg     600
tctctttccc cagctctggg accacctttg aagtgatcct atttatttat ttatttatat     660
ttatttttat ttttattttt taatttattt tgttgttttt ctacaagact gtttcttatc     720
ttggagcaca aacttgccac aacataataa acatagcgta tttcctgctt ttgaaaagga     780
aaaaaaaaa aaaaaaa                                                     797

<210> SEQ ID NO 8
<211> LENGTH: 121
<212> TYPE: PRT
<213> ORGANISM: Mus musculus

<400> SEQUENCE: 8

Met Asp Leu Leu Lys Val Leu Ser Gln Met Ile Leu Phe Leu Leu Phe
1               5                   10                  15

Leu Tyr Leu Ser Pro Leu Gly Gly His Ser Tyr Pro Leu Gly Ser Pro
            20                  25                  30

Ser Gln Ser Pro Glu Gln Phe Lys Met Gln Lys Leu Leu Glu Leu Ile
        35                  40                  45

Arg Glu Lys Ser Glu Glu Met Ala Gln Arg Leu Leu Lys Asp Gln
    50                  55                  60

Gly Leu Thr Lys Glu His Pro Lys Arg Val Leu Arg Ser Gln Gly Ser
65                  70                  75                  80

Thr Leu Arg Val Gln Gln Arg Pro Gln Asn Ser Lys Val Thr His Ile
            85                  90                  95
```

Ser Ser Cys Phe Gly His Lys Ile Asp Arg Ile Gly Ser Val Ser Arg
            100                 105                 110

Leu Gly Cys Asn Ala Leu Lys Leu Leu
        115                 120

<210> SEQ ID NO 9
<211> LENGTH: 4065
<212> TYPE: DNA
<213> ORGANISM: Mus musculus

<400> SEQUENCE: 9

| | | | | | |
|---|---|---|---|---|---|
| atactcctgg | ggcaagcgcg | agcgcacact | cccctttcct | cgctggcgca | cccgctcccc | 60 |
| tcgctcttct | tagatcgccc | tctcgttctc | tcgctctcca | cggactccct | tcgggtgctg | 120 |
| cgctcgctct | cacctgctct | aaagcaccct | ccgctctcgg | acgctcccaa | ttccgcgctc | 180 |
| ctgctcgacg | gcgggacagt | cgcagcctcg | gcaggcagct | tgctctcgcc | gctgcggctt | 240 |
| caacccagcc | ccctccctcg | ctacggctcg | ggcgctcttg | actcccgacc | ctcgcctctg | 300 |
| agcccgagga | cggcgatcag | accatggtga | cagcgctgct | ccgtcgctgc | gctcgctgag | 360 |
| gccatgccgg | gttcccgacg | cgtccgtccg | cgcctaaggg | cgctgctgct | gctaccgccg | 420 |
| ctgctgctgc | tccgaagcgg | ccacgcgagc | gacctgaccg | tggccgtggt | gctgccgctg | 480 |
| accaacacct | cgtacccgtg | gtcttgggcg | cgtgtagggc | cggcggtgga | actggctctc | 540 |
| gggagggtga | aggctcggcc | ggacttgctg | ccgggttgga | cggtccgtat | ggtgctgggc | 600 |
| agcagcgaga | acgcggcggg | cgtctgctcc | gacaccgctg | caccgctggc | cgcggtggat | 660 |
| ctcaagtggg | agcacagccc | cgcggtgttc | ctgggccccg | gctgcgtata | tctgctgcc | 720 |
| ccggtgggac | gcttcaccgc | gcactggcgg | gtgccgctgc | tgacggctgg | cgccccggct | 780 |
| ctgggcatcg | gggtgaagga | tgagtacgcg | ttaaccaccc | gcacaggacc | cagccatgtc | 840 |
| aagctgggcg | acttcgtgac | ggcgctgcat | cgacggctgg | gctgggagca | ccaggcgctt | 900 |
| gtgctctatg | cagatcggct | gggcgacgac | cggccgtgct | tcttcatagt | ggaggggctg | 960 |
| tacatgcggg | tgcgtgagcg | actcaacatc | acagtaaatc | accaggagtt | cgtcgagggc | 1020 |
| gacccggacc | actacaccaa | gctactgcgg | accgtgcagc | gcaagggcag | agttatctac | 1080 |
| atctgcagtt | ctccggatgc | cttcaggaat | ctgatgcttt | tggccctgga | tgctggcctg | 1140 |
| actggggagg | actatgtttt | cttccacctg | gatgtgtttg | gcaaagcct | tcagggtgct | 1200 |
| cagggccctg | ttcccaggaa | gccctgggaa | agagacgatg | ggcaggatag | gagagcccgc | 1260 |
| caggcctttc | aggctgccaa | aattattact | tacaaagaac | ccgataatcc | tgagtacttg | 1320 |
| gaattcctga | agcagctaaa | actcttggct | gacaagaaat | tcaacttcac | catggaggat | 1380 |
| ggcctgaaaa | atatcatccc | agcatccttc | catgacgggc | tcctgctcta | tgtccaggca | 1440 |
| gtgacagaga | ctctggcaca | gggggcact | gtcactgatg | gagagaacat | cactcagcgg | 1500 |
| atgtggaacc | gaagcttcca | aggtgtgaca | ggatacctga | aaattgatag | aaatggagat | 1560 |
| cgggacactg | atttctccct | ctgggatatg | accccgaga | caggtgcctt | cagggttgtc | 1620 |
| ctgaacttta | atggtacttc | ccaggagctg | atggctgtgt | cagaacacag | attatactgg | 1680 |
| cctctgggat | acccacctcc | tgacatccct | aaatgtggct | tgacaatga | ggacccagcc | 1740 |
| tgcaaccaag | accactttc | cacactggag | gttctggctt | tggtgggcag | cctctctctg | 1800 |
| gttagctttc | tgatcgtgtc | tttcttcata | tacaggaaga | tgcagctgga | aaaggagctg | 1860 |
| gtctcagagt | tgtggcgggt | gcgctgggag | gacttgcagc | ccagcagcct | ggagaggcac | 1920 |

| | | | |
|---|---|---|---|
| cttcggagcg | ctggcagtcg gctgaccctg agtgggcgag gctccaatta tggctccctg | | 1980 |
| ctaaccacgg | agggccagtt ccaagtcttt gccaagacag catactataa gggcaacctc | | 2040 |
| gtggctgtga | acgtgtgaac cggaaacgc attgagttga cacgaaaagt cctgtttgaa | | 2100 |
| cttaaacata | tgcgggatgt gcagaatgag cacttgacca gatttgtggg agcttgtacc | | 2160 |
| gaccctccca | acatctgtat cctcacagag tactgtcccc gtgggagcct acaggacatt | | 2220 |
| ctagagaatg | agagtattac cctggactgg atgtttcggt actcactcac caatgacatt | | 2280 |
| gtcaagggaa | tgctctttct acacaacggg gccattggtt cccatgggaa cctcaagtca | | 2340 |
| tccaactgcg | tggtagatgg acgttttgtg ttaaagatca cagactatgg gctcgagagc | | 2400 |
| ttcagagacc | cggagccaga gcaaggacac accctctttg ccaaaaaact gtggactgca | | 2460 |
| cctgagctcc | tgcgaatggc ttccccacct gcccgtggct cccaagctgg ggatgtctac | | 2520 |
| agttttggta | tcatccttca ggaaattgcc ctaagaagtg gggtcttcta tgtggaaggt | | 2580 |
| ttggacctca | gcccaaaaga gatcattgag cgtgtgactc ggggcgagca gccccattc | | 2640 |
| cgaccttcca | tggatctgca gagccacctg gaggaactgg ggcagctgat gcagaggtgc | | 2700 |
| tgggcagagg | atcctcagga gcggccaccc tttcaacaga tccgcctggc gctgcgcaag | | 2760 |
| ttcaacaagg | agaacagcag caacatcctg gacaacctgc tgtcacgcat ggaacagtac | | 2820 |
| gccaacaacc | tggaggaact ggtagaggag agaacacagg cttatctgga ggagaagcgc | | 2880 |
| aaagctgagg | ccctgcttta ccagattctg cctcactctg tggctgagca gctgaagaga | | 2940 |
| ggcgagacag | tccaggctga ggcatttgat agtgttacta tctatttcag tgatatcgtg | | 3000 |
| ggctttacag | ctctttcagc agagagcaca cccatgcagg tggtcaccct gctcaatgat | | 3060 |
| ctgtacacct | gttttgatgc tgtcatagac aactttgatg tgtacaaggt agagaccatt | | 3120 |
| ggtgatgctt | acatggtggt atcagggctc ccagtgagga atggacagct ccatgcccga | | 3180 |
| gaggtagccc | gaatggcact tgcactgctc gatgctgtac gctccttccg catccgccat | | 3240 |
| aggccccagg | aacagctgcg cttgcgcatt ggaattcaca caggtcccgt gtgtgctggt | | 3300 |
| gtggtagggc | taaagatgcc ccgatactgc ctctttggag acacagtcaa cacagcttca | | 3360 |
| agaatggagt | ctaatgggga agccctcagg atccacttgt cttcggagac caaggctgtg | | 3420 |
| ctggaagagt | tcgatggttt tgagctggag ctccgaggtg acgtggaaat gaagggcaaa | | 3480 |
| ggcaaggttc | gaacctattg gctcctcggg gagcggggat gcagcactcg aggctgacct | | 3540 |
| actgccctgc | tattccttgt cacctcccct ccctgtgcca gcaatgacac gggtgtccaa | | 3600 |
| cttccgcctc | tcccacagca gctcagccac tgtggaaaga ttagggacct aaccagcgca | | 3660 |
| gtcatcagat | gtgacctctg agagaggatg gagatggtgg ggactggagg gggactccta | | 3720 |
| agtttatagg | gctgactgaa atacccagtc actcccgtag cacatgcccc gcccccccc | | 3780 |
| cgcccccca | ctcagctgcc tagcagacag tgattccttc tgccgccctc aacttagctc | | 3840 |
| cactgtgact | tagagggagg gaaattgcca cctgaaggaa agagaaaaga gattctcggg | | 3900 |
| gtttgcagga | ggcaggcagt cctgtgtcac aaatactccc ctcactccca gtccaccacc | | 3960 |
| tgccccaccg | acttcccttc ccacacagtg cactgaggag aagagaggca tggggttgcc | | 4020 |
| ttgcttctcc | tatgagcaaa acccattaaa gtctttattc ctgtg | | 4065 |

<210> SEQ ID NO 10
<211> LENGTH: 1057
<212> TYPE: PRT
<213> ORGANISM: Mus musculus

<400> SEQUENCE: 10

-continued

```
Met Pro Gly Ser Arg Val Arg Pro Arg Leu Arg Ala Leu Leu Leu
 1               5                  10                  15

Leu Pro Pro Leu Leu Leu Arg Ser Gly His Ala Ser Asp Leu Thr
            20                  25                  30

Val Ala Val Val Leu Pro Leu Thr Asn Thr Ser Tyr Pro Trp Ser Trp
        35                  40                  45

Ala Arg Val Gly Pro Ala Val Glu Leu Ala Leu Gly Arg Val Lys Ala
    50                  55                  60

Arg Pro Asp Leu Leu Pro Gly Trp Thr Val Arg Met Val Leu Gly Ser
65                  70                  75                  80

Ser Glu Asn Ala Ala Gly Val Cys Ser Asp Thr Ala Ala Pro Leu Ala
                85                  90                  95

Ala Val Asp Leu Lys Trp Glu His Ser Pro Ala Val Phe Leu Gly Pro
            100                 105                 110

Gly Cys Val Tyr Ser Ala Ala Pro Val Gly Arg Phe Thr Ala His Trp
        115                 120                 125

Arg Val Pro Leu Leu Thr Ala Gly Ala Pro Ala Leu Gly Ile Gly Val
    130                 135                 140

Lys Asp Glu Tyr Ala Leu Thr Thr Arg Thr Gly Pro Ser His Val Lys
145                 150                 155                 160

Leu Gly Asp Phe Val Thr Ala Leu His Arg Arg Leu Gly Trp Glu His
                165                 170                 175

Gln Ala Leu Val Leu Tyr Ala Asp Arg Leu Gly Asp Asp Arg Pro Cys
            180                 185                 190

Phe Phe Ile Val Glu Gly Leu Tyr Met Arg Val Arg Glu Arg Leu Asn
        195                 200                 205

Ile Thr Val Asn His Gln Glu Phe Val Glu Gly Asp Pro Asp His Tyr
    210                 215                 220

Thr Lys Leu Leu Arg Thr Val Gln Arg Lys Gly Arg Val Ile Tyr Ile
225                 230                 235                 240

Cys Ser Ser Pro Asp Ala Phe Arg Asn Leu Met Leu Leu Ala Leu Asp
                245                 250                 255

Ala Gly Leu Thr Gly Glu Asp Tyr Val Phe Phe His Leu Asp Val Phe
            260                 265                 270

Gly Gln Ser Leu Gln Gly Ala Gln Gly Pro Val Pro Arg Lys Pro Trp
        275                 280                 285

Glu Arg Asp Asp Gly Gln Asp Arg Arg Ala Arg Gln Ala Phe Gln Ala
    290                 295                 300

Ala Lys Ile Ile Thr Tyr Lys Glu Pro Asp Asn Pro Glu Tyr Leu Glu
305                 310                 315                 320

Phe Leu Lys Gln Leu Lys Leu Leu Ala Asp Lys Lys Phe Asn Phe Thr
                325                 330                 335

Met Glu Asp Gly Leu Lys Asn Ile Ile Pro Ala Ser Phe His Asp Gly
            340                 345                 350

Leu Leu Leu Tyr Val Gln Ala Val Thr Glu Thr Leu Ala Gln Gly Gly
        355                 360                 365

Thr Val Thr Asp Gly Glu Asn Ile Thr Gln Arg Met Trp Asn Arg Ser
    370                 375                 380

Phe Gln Gly Val Thr Gly Tyr Leu Lys Ile Asp Arg Asn Gly Asp Arg
385                 390                 395                 400

Asp Thr Asp Phe Ser Leu Trp Asp Met Asp Pro Glu Thr Gly Ala Phe
                405                 410                 415
```

```
Arg Val Val Leu Asn Phe Asn Gly Thr Ser Gln Glu Leu Met Ala Val
                420                 425                 430

Ser Glu His Arg Leu Tyr Trp Pro Leu Gly Tyr Pro Pro Asp Ile
        435                 440                 445

Pro Lys Cys Gly Phe Asp Asn Glu Asp Pro Ala Cys Asn Gln Asp His
    450                 455                 460

Phe Ser Thr Leu Glu Val Leu Ala Leu Val Gly Ser Leu Ser Leu Val
465                 470                 475                 480

Ser Phe Leu Ile Val Ser Phe Ile Tyr Arg Lys Met Gln Leu Glu
                485                 490                 495

Lys Glu Leu Val Ser Glu Leu Trp Arg Val Arg Trp Glu Asp Leu Gln
            500                 505                 510

Pro Ser Ser Leu Glu Arg His Leu Arg Ser Ala Gly Ser Arg Leu Thr
            515                 520                 525

Leu Ser Gly Arg Gly Ser Asn Tyr Gly Ser Leu Leu Thr Thr Glu Gly
            530                 535                 540

Gln Phe Gln Val Phe Ala Lys Thr Ala Tyr Tyr Lys Gly Asn Leu Val
545                 550                 555                 560

Ala Val Lys Arg Val Asn Arg Lys Arg Ile Glu Leu Thr Arg Lys Val
                565                 570                 575

Leu Phe Glu Leu Lys His Met Arg Asp Val Gln Asn Glu His Leu Thr
            580                 585                 590

Arg Phe Val Gly Ala Cys Thr Asp Pro Pro Asn Ile Cys Ile Leu Thr
            595                 600                 605

Glu Tyr Cys Pro Arg Gly Ser Leu Gln Asp Ile Leu Glu Asn Glu Ser
        610                 615                 620

Ile Thr Leu Asp Trp Met Phe Arg Tyr Ser Leu Thr Asn Asp Ile Val
625                 630                 635                 640

Lys Gly Met Leu Phe Leu His Asn Gly Ala Ile Gly Ser His Gly Asn
                645                 650                 655

Leu Lys Ser Ser Asn Cys Val Val Asp Gly Arg Phe Val Leu Lys Ile
            660                 665                 670

Thr Asp Tyr Gly Leu Glu Ser Phe Arg Asp Pro Glu Pro Glu Gln Gly
            675                 680                 685

His Thr Leu Phe Ala Lys Lys Leu Trp Thr Ala Pro Glu Leu Leu Arg
        690                 695                 700

Met Ala Ser Pro Pro Ala Arg Gly Ser Gln Ala Gly Asp Val Tyr Ser
705                 710                 715                 720

Phe Gly Ile Ile Leu Gln Glu Ile Ala Leu Arg Ser Gly Val Phe Tyr
                725                 730                 735

Val Glu Gly Leu Asp Leu Ser Pro Lys Glu Ile Ile Glu Arg Val Thr
            740                 745                 750

Arg Gly Glu Gln Pro Pro Phe Arg Pro Ser Met Asp Leu Gln Ser His
        755                 760                 765

Leu Glu Glu Leu Gly Gln Leu Met Gln Arg Cys Trp Ala Glu Asp Pro
    770                 775                 780

Gln Glu Arg Pro Pro Phe Gln Gln Ile Arg Leu Ala Leu Arg Lys Phe
785                 790                 795                 800

Asn Lys Glu Asn Ser Ser Asn Ile Leu Asp Asn Leu Leu Ser Arg Met
                805                 810                 815

Glu Gln Tyr Ala Asn Asn Leu Glu Glu Leu Val Glu Glu Arg Thr Gln
            820                 825                 830

Ala Tyr Leu Glu Glu Lys Arg Lys Ala Glu Ala Leu Leu Tyr Gln Ile
```

-continued

```
               835                 840                 845
Leu Pro His Ser Val Ala Glu Gln Leu Lys Arg Gly Glu Thr Val Gln
    850                 855                 860

Ala Glu Ala Phe Asp Ser Val Thr Ile Tyr Phe Ser Asp Ile Val Gly
865                 870                 875                 880

Phe Thr Ala Leu Ser Ala Glu Ser Thr Pro Met Gln Val Val Thr Leu
                885                 890                 895

Leu Asn Asp Leu Tyr Thr Cys Phe Asp Ala Val Ile Asp Asn Phe Asp
            900                 905                 910

Val Tyr Lys Val Glu Thr Ile Gly Asp Ala Tyr Met Val Val Ser Gly
        915                 920                 925

Leu Pro Val Arg Asn Gly Gln Leu His Ala Arg Glu Val Ala Arg Met
    930                 935                 940

Ala Leu Ala Leu Leu Asp Ala Val Arg Ser Phe Arg Ile Arg His Arg
945                 950                 955                 960

Pro Gln Glu Gln Leu Arg Leu Arg Ile Gly Ile His Thr Gly Pro Val
                965                 970                 975

Cys Ala Gly Val Val Gly Leu Lys Met Pro Arg Tyr Cys Leu Phe Gly
                980                 985                 990

Asp Thr Val Asn Thr Ala Ser Arg Met Glu Ser Asn Gly Glu Ala Leu
            995                1000                1005

Arg Ile His Leu Ser Ser Glu Thr Lys Ala Val Leu Glu Glu Phe
    1010                1015                1020

Asp Gly Phe Glu Leu Glu Leu Arg Gly Asp Val Glu Met Lys Gly
    1025                1030                1035

Lys Gly Lys Val Arg Thr Tyr Trp Leu Leu Gly Glu Arg Gly Cys
    1040                1045                1050

Ser Thr Arg Gly
    1055
```